United States Patent
Stahmann

(10) Patent No.: US 12,329,500 B2
(45) Date of Patent: Jun. 17, 2025

(54) IMPLANTABLE PASSIVE MEAN PRESSURE SENSOR

(71) Applicant: BOSTON SCIENTIFIC SCIMED, INC., Maple Grove, MN (US)

(72) Inventor: Jeffrey E. Stahmann, Ramsey, MN (US)

(73) Assignee: BOSTON SCIENTIFIC SCIMED, INC.

( * ) Notice: Subject to any disclaimer, the term of this patent is extended or adjusted under 35 U.S.C. 154(b) by 769 days.

(21) Appl. No.: 17/536,820

(22) Filed: Nov. 29, 2021

(65) Prior Publication Data

US 2022/0167861 A1  Jun. 2, 2022

Related U.S. Application Data

(60) Provisional application No. 63/119,337, filed on Nov. 30, 2020.

(51) Int. Cl.
*A61B 5/021* (2006.01)
*A61B 5/00* (2006.01)
*G01L 19/08* (2006.01)

(52) U.S. Cl.
CPC ........ *A61B 5/02125* (2013.01); *A61B 5/0031* (2013.01); *G01L 19/08* (2013.01)

(58) Field of Classification Search
CPC .............. A61B 5/02125; A61B 5/0031; A61B 2017/00022; A61B 17/12122;
(Continued)

(56) References Cited

U.S. PATENT DOCUMENTS

| | | |
|---|---|---|
| 178,283 A | 6/1876 | French |
| 1,967,318 A | 7/1934 | Monahan |

(Continued)

FOREIGN PATENT DOCUMENTS

| | | |
|---|---|---|
| CN | 1399571 A | 2/2003 |
| CN | 202143640 U | 2/2012 |

(Continued)

OTHER PUBLICATIONS

International Search Report and Written Opinion dated Aug. 3, 2004 for International Application No. PCT/US2004/008109.

(Continued)

*Primary Examiner* — Rene T Towa
*Assistant Examiner* — Matthew Eric Ogles
(74) *Attorney, Agent, or Firm* — Seager, Tufte & Wickhem LLP

(57) ABSTRACT

An implantable pressure sensor includes a housing and a sensing component that is housed by the housing and exposed to an external pressure that is exterior to the housing. In response to the external pressure, the sensing component is configured to undergo a physical transformation that is representative of a mean pressure of the external pressure over a period of time of at least one minute. The pressure sensor includes circuitry that is operatively coupled to the sensing component and that is responsive to the physical transformation of the sensing component to produce a mean pressure signal that is representative of the mean pressure of the external pressure over the period of time.

19 Claims, 7 Drawing Sheets

(58) Field of Classification Search
CPC ........ A61B 17/12172; A61B 17/12177; A61B 2560/0219; A61B 5/07; A61B 5/205; A61B 5/0215; A61B 17/12031; A61B 17/12131; A61B 5/021; A61B 5/03; A61B 5/023; A61B 5/031; A61B 5/033; A61B 2562/0247; A61B 5/02154; A61B 5/0235; A61B 5/02427; A61B 5/02141; A61B 2562/0214; A61B 2562/02; A61B 2562/168; G01L 19/08

See application file for complete search history.

(56) References Cited

U.S. PATENT DOCUMENTS

| | | |
|---|---|---|
| 3,402,710 A | 9/1968 | Paleschuck |
| 3,540,431 A | 11/1970 | Mobin-Uddin |
| 3,557,794 A | 1/1971 | Van Patten |
| 3,638,652 A | 2/1972 | Kelley |
| 3,811,449 A | 5/1974 | Gravlee et al. |
| 3,844,302 A | 10/1974 | Klein |
| 3,874,388 A | 4/1975 | King et al. |
| 4,007,743 A | 2/1977 | Blake |
| 4,108,420 A | 8/1978 | West et al. |
| 4,175,545 A | 11/1979 | Termanini |
| 4,309,776 A | 1/1982 | Berguer |
| 4,341,218 A | 7/1982 | Ü |
| 4,364,392 A | 12/1982 | Strother et al. |
| 4,425,908 A | 1/1984 | Simon |
| 4,545,367 A | 10/1985 | Tucci |
| 4,585,000 A | 4/1986 | Hershenson |
| 4,603,693 A | 8/1986 | Conta et al. |
| 4,611,594 A | 9/1986 | Grayhack et al. |
| 4,619,246 A | 10/1986 | Molgaard-Nielsen et al. |
| 4,638,803 A | 1/1987 | Rand et al. |
| 4,665,906 A | 5/1987 | Jervis |
| 4,681,588 A | 7/1987 | Ketharanathan et al. |
| 4,710,192 A | 12/1987 | Liotta et al. |
| 4,718,417 A | 1/1988 | Kittrell et al. |
| 4,759,348 A | 7/1988 | Cawood et al. |
| 4,781,177 A | 11/1988 | Lebigot |
| 4,793,348 A | 12/1988 | Palmaz |
| 4,827,907 A | 5/1989 | Tashiro |
| 4,832,055 A | 5/1989 | Palestrant |
| 4,873,978 A | 10/1989 | Ginsburg |
| 4,899,751 A | 2/1990 | Cohen |
| 4,917,089 A | 4/1990 | Sideris |
| 4,921,484 A | 5/1990 | Hillstead |
| 4,960,412 A | 10/1990 | Fink |
| 4,966,150 A | 10/1990 | Etienne et al. |
| 4,998,972 A | 3/1991 | Chin et al. |
| 5,037,810 A | 8/1991 | Saliba, Jr. |
| 5,041,090 A | 8/1991 | Scheglov et al. |
| 5,041,093 A | 8/1991 | Chu |
| 5,042,707 A | 8/1991 | Taheri |
| 5,053,009 A | 10/1991 | Herzberg |
| 5,064,435 A | 11/1991 | Porter |
| 5,071,407 A | 12/1991 | Termin et al. |
| 5,078,736 A | 1/1992 | Behl |
| 5,098,440 A | 3/1992 | Hillstead |
| 5,108,418 A | 4/1992 | Lefebvre |
| 5,108,420 A | 4/1992 | Marks |
| 5,108,474 A | 4/1992 | Riedy et al. |
| 5,116,360 A | 5/1992 | Pinchuk et al. |
| 5,122,136 A | 6/1992 | Guglielmi et al. |
| 5,129,394 A | 7/1992 | Mehra |
| 5,171,259 A | 12/1992 | Inoue |
| 5,171,383 A | 12/1992 | Sagaye et al. |
| 5,176,692 A | 1/1993 | Wilk et al. |
| 5,192,301 A | 3/1993 | Kamiya et al. |
| 5,211,658 A | 5/1993 | Clouse |
| 5,234,458 A | 8/1993 | Metais |
| 5,256,146 A | 10/1993 | Ensminger et al. |
| 5,258,000 A | 11/1993 | Gianturco |
| 5,258,042 A | 11/1993 | Mehta |
| 5,279,539 A | 1/1994 | Bohan et al. |
| 5,284,488 A | 2/1994 | Sideris |
| 5,304,184 A | 4/1994 | Hathaway et al. |
| 5,306,234 A | 4/1994 | Johnson |
| 5,312,341 A | 5/1994 | Turi |
| 5,329,942 A | 7/1994 | Gunther et al. |
| 5,334,217 A | 8/1994 | Das |
| 5,344,439 A | 9/1994 | Otten |
| 5,350,398 A | 9/1994 | Pavcnik et al. |
| 5,350,399 A | 9/1994 | Erlebacher et al. |
| 5,353,784 A | 10/1994 | Nady-Mohamed |
| 5,366,460 A | 11/1994 | Eberbach |
| 5,366,504 A | 11/1994 | Andersen et al. |
| 5,370,657 A | 12/1994 | Irie |
| 5,375,612 A | 12/1994 | Cottenceau et al. |
| 5,397,331 A | 3/1995 | Himpens et al. |
| 5,397,355 A | 3/1995 | Marin et al. |
| 5,409,444 A | 4/1995 | Kensey et al. |
| 5,417,699 A | 5/1995 | Klein et al. |
| 5,421,832 A | 6/1995 | Lefebvre |
| 5,425,744 A | 6/1995 | Fagan et al. |
| 5,427,119 A | 6/1995 | Swartz et al. |
| 5,433,727 A | 7/1995 | Sideris |
| 5,443,454 A | 8/1995 | Tanabe et al. |
| 5,443,478 A | 8/1995 | Purdy et al. |
| 5,451,235 A | 9/1995 | Lock et al. |
| 5,454,365 A | 10/1995 | Bonutti |
| 5,464,408 A | 11/1995 | Duc |
| 5,469,867 A | 11/1995 | Schmitt |
| 5,490,856 A | 2/1996 | Person et al. |
| 5,497,774 A | 3/1996 | Swartz et al. |
| 5,499,975 A | 3/1996 | Cope et al. |
| 5,499,995 A | 3/1996 | Teirstein |
| 5,522,790 A | 6/1996 | Voll et al. |
| 5,522,822 A | 6/1996 | Phelps et al. |
| 5,522,836 A | 6/1996 | Palermo |
| 5,527,322 A | 6/1996 | Klein et al. |
| 5,527,338 A | 6/1996 | Purdy |
| 5,558,093 A | 9/1996 | Pomeranz et al. |
| 5,558,652 A | 9/1996 | Henke |
| 5,569,204 A | 10/1996 | Cramer et al. |
| 5,591,196 A | 1/1997 | Marin et al. |
| 5,614,204 A | 3/1997 | Cochrum |
| 5,634,936 A | 6/1997 | Linden et al. |
| 5,634,942 A | 6/1997 | Chevillon et al. |
| 5,637,097 A | 6/1997 | Yoon |
| 5,643,282 A | 7/1997 | Kieturakis |
| 5,643,292 A | 7/1997 | Hart |
| 5,649,953 A | 7/1997 | Lefebvre |
| 5,653,690 A | 8/1997 | Booth et al. |
| 5,662,671 A | 9/1997 | Barbut et al. |
| 5,669,933 A | 9/1997 | Simon et al. |
| 5,681,345 A | 10/1997 | Euteneuer |
| 5,681,347 A | 10/1997 | Cathcart et al. |
| 5,683,411 A | 11/1997 | Kavteladze et al. |
| 5,690,671 A | 11/1997 | McGurk et al. |
| 5,693,067 A | 12/1997 | Purdy |
| 5,693,886 A * | 12/1997 | Seimiya ............... G01L 1/142 73/718 |
| 5,695,525 A | 12/1997 | Mulhauser et al. |
| 5,700,285 A | 12/1997 | Myers et al. |
| 5,702,421 A | 12/1997 | Schneidt |
| 5,704,910 A | 1/1998 | Humes |
| 5,709,224 A | 1/1998 | Behl et al. |
| 5,709,704 A | 1/1998 | Nott et al. |
| 5,709,707 A | 1/1998 | Lock et al. |
| 5,722,400 A | 3/1998 | Ockuly et al. |
| 5,724,975 A | 3/1998 | Negus et al. |
| 5,725,512 A | 3/1998 | Swartz et al. |
| 5,725,552 A | 3/1998 | Kotula et al. |
| 5,725,568 A | 3/1998 | Hastings |
| 5,733,294 A | 3/1998 | Forber et al. |
| 5,733,302 A | 3/1998 | Myler et al. |
| 5,735,290 A | 4/1998 | Sterman et al. |
| 5,749,880 A | 5/1998 | Banas et al. |
| 5,749,883 A | 5/1998 | Halpern |
| 5,749,894 A | 5/1998 | Engelson |
| 5,766,219 A | 6/1998 | Horton |
| 5,766,246 A | 6/1998 | Mulhauser et al. |
| 5,769,816 A | 6/1998 | Barbut et al. |

(56) References Cited

U.S. PATENT DOCUMENTS

| | | |
|---|---|---|
| 5,776,097 A | 7/1998 | Massoud |
| 5,776,162 A | 7/1998 | Kleshinski |
| 5,782,860 A | 7/1998 | Epstein et al. |
| 5,785,679 A | 7/1998 | Abolfathi et al. |
| 5,800,454 A | 9/1998 | Jacobsen et al. |
| 5,800,457 A | 9/1998 | Gelbfish |
| 5,800,512 A | 9/1998 | Letnz et al. |
| 5,807,261 A | 9/1998 | Benaron et al. |
| 5,810,874 A | 9/1998 | Lefebvre |
| 5,814,028 A | 9/1998 | Swartz et al. |
| 5,814,029 A | 9/1998 | Hassett |
| 5,814,064 A | 9/1998 | Daniel |
| 5,820,591 A | 10/1998 | Thompson et al. |
| 5,823,198 A | 10/1998 | Jones et al. |
| 5,830,228 A | 11/1998 | Knapp et al. |
| 5,833,673 A | 11/1998 | Ockuly et al. |
| 5,836,913 A | 11/1998 | Orth et al. |
| 5,836,968 A | 11/1998 | Simon et al. |
| 5,840,027 A | 11/1998 | Swartz et al. |
| 5,843,118 A | 12/1998 | Sepetka et al. |
| 5,846,260 A | 12/1998 | Maahs |
| 5,846,261 A | 12/1998 | Kotula et al. |
| 5,848,969 A | 12/1998 | Panescu et al. |
| 5,849,005 A | 12/1998 | Garrison et al. |
| 5,851,232 A | 12/1998 | Lois |
| 5,853,422 A | 12/1998 | Huebsch et al. |
| 5,855,597 A | 1/1999 | Jayaraman |
| 5,865,791 A | 2/1999 | Whayne et al. |
| 5,865,802 A | 2/1999 | Yoon et al. |
| 5,868,702 A | 2/1999 | Stevens et al. |
| 5,868,708 A | 2/1999 | Hart et al. |
| 5,876,367 A | 3/1999 | Kaganov et al. |
| 5,879,296 A | 3/1999 | Ockuly et al. |
| 5,879,366 A | 3/1999 | Shaw et al. |
| 5,882,340 A | 3/1999 | Yoon |
| 5,885,258 A | 3/1999 | Sachdeva et al. |
| 5,891,558 A | 4/1999 | Bell et al. |
| 5,895,399 A | 4/1999 | Barbut et al. |
| 5,902,289 A | 5/1999 | Swartz et al. |
| 5,904,680 A | 5/1999 | Kordis et al. |
| 5,904,703 A | 5/1999 | Gilson |
| 5,906,207 A | 5/1999 | Shen |
| 5,910,154 A | 6/1999 | Tsugita et al. |
| 5,911,734 A | 6/1999 | Tsugita et al. |
| 5,916,236 A | 6/1999 | Muijs Van de Moer et al. |
| 5,925,060 A | 7/1999 | Forber |
| 5,925,063 A | 7/1999 | Khosravi |
| 5,925,074 A | 7/1999 | Gingras et al. |
| 5,925,075 A | 7/1999 | Myers et al. |
| 5,928,192 A | 7/1999 | Maahs |
| 5,928,260 A | 7/1999 | Chin et al. |
| 5,931,818 A | 8/1999 | Werp et al. |
| 5,935,145 A | 8/1999 | Villar et al. |
| 5,935,147 A | 8/1999 | Kensey et al. |
| 5,935,148 A | 8/1999 | Villar et al. |
| 5,941,249 A | 8/1999 | Maynard |
| 5,941,896 A | 8/1999 | Kerr |
| 5,944,738 A | 8/1999 | Amplatz et al. |
| 5,947,997 A | 9/1999 | Pavcnik et al. |
| 5,951,589 A | 9/1999 | Epstein et al. |
| 5,951,599 A | 9/1999 | McCrory |
| 5,954,694 A | 9/1999 | Sunseri |
| 5,954,767 A | 9/1999 | Pajotin et al. |
| 5,957,940 A | 9/1999 | Tanner et al. |
| 5,961,545 A | 10/1999 | Entz et al. |
| 5,976,174 A | 11/1999 | Ruiz |
| 5,980,514 A | 11/1999 | Kupiecki et al. |
| 5,980,555 A | 11/1999 | Barbut et al. |
| 5,989,281 A | 11/1999 | Barbut et al. |
| 5,993,469 A | 11/1999 | McKenzie et al. |
| 5,993,483 A | 11/1999 | Gianotti |
| 5,997,557 A | 12/1999 | Barbut et al. |
| 6,004,280 A | 12/1999 | Buck et al. |
| 6,004,348 A | 12/1999 | Banas et al. |
| 6,007,523 A | 12/1999 | Mangosong |
| 6,007,557 A | 12/1999 | Ambrisco et al. |
| 6,010,517 A | 1/2000 | Baccaro |
| 6,010,522 A | 1/2000 | Barbut et al. |
| 6,013,093 A | 1/2000 | Nott et al. |
| 6,024,751 A | 2/2000 | Lovato et al. |
| 6,024,754 A | 2/2000 | Engelson |
| 6,024,755 A | 2/2000 | Addis |
| 6,024,756 A | 2/2000 | Huebsch et al. |
| 6,027,520 A | 2/2000 | Tsugita et al. |
| 6,033,420 A | 3/2000 | Hahnen |
| 6,036,720 A | 3/2000 | Abrams et al. |
| 6,042,598 A | 3/2000 | Tsugita et al. |
| 6,048,331 A | 4/2000 | Tsugita et al. |
| 6,051,014 A | 4/2000 | Jang |
| 6,051,015 A | 4/2000 | Maahs |
| 6,056,720 A | 5/2000 | Morse |
| 6,063,070 A | 5/2000 | Eder |
| 6,063,113 A | 5/2000 | Kavteladze et al. |
| 6,066,126 A | 5/2000 | Li et al. |
| 6,068,621 A | 5/2000 | Balceta et al. |
| 6,074,357 A | 6/2000 | Kaganov et al. |
| 6,076,012 A | 6/2000 | Swanson et al. |
| 6,079,414 A | 6/2000 | Roth |
| 6,080,182 A | 6/2000 | Shaw et al. |
| 6,080,183 A | 6/2000 | Tsugita et al. |
| 6,083,239 A | 7/2000 | Addis |
| 6,090,084 A | 7/2000 | Hassett et al. |
| 6,096,052 A | 8/2000 | Callister et al. |
| 6,096,053 A | 8/2000 | Bates et al. |
| 6,110,243 A | 8/2000 | Wnenchak et al. |
| 6,123,715 A | 9/2000 | Amplatz |
| 6,124,523 A | 9/2000 | Banas et al. |
| 6,132,438 A | 10/2000 | Fleischman et al. |
| 6,135,991 A | 10/2000 | Muni et al. |
| 6,136,016 A | 10/2000 | Barbut et al. |
| 6,139,527 A | 10/2000 | Laufer et al. |
| 6,139,573 A | 10/2000 | Sogard et al. |
| 6,152,144 A | 11/2000 | Lesh et al. |
| 6,152,946 A | 11/2000 | Broome et al. |
| 6,156,055 A | 12/2000 | Ravenscroft |
| 6,159,195 A | 12/2000 | Ha et al. |
| 6,161,543 A | 12/2000 | Cox et al. |
| 6,168,615 B1 | 1/2001 | Ken et al. |
| 6,171,329 B1 | 1/2001 | Shaw et al. |
| 6,179,859 B1 | 1/2001 | Bates et al. |
| 6,193,739 B1 | 2/2001 | Chevillon et al. |
| 6,203,531 B1 | 3/2001 | Ockuly et al. |
| 6,206,907 B1 | 3/2001 | Marino et al. |
| 6,214,029 B1 | 4/2001 | Thill et al. |
| 6,221,092 B1 | 4/2001 | Koike et al. |
| 6,231,561 B1 | 5/2001 | Frazier et al. |
| 6,231,589 B1 | 5/2001 | Wessman et al. |
| 6,235,045 B1 | 5/2001 | Barbut et al. |
| 6,245,012 B1 | 6/2001 | Kleshinski |
| 6,251,122 B1 | 6/2001 | Tsukernik |
| 6,258,115 B1 | 7/2001 | Dubrul |
| 6,267,772 B1 | 7/2001 | Mulhauser et al. |
| 6,267,776 B1 | 7/2001 | O'Connell |
| 6,270,490 B1 | 8/2001 | Hahnen |
| 6,270,530 B1 | 8/2001 | Eldridge et al. |
| 6,270,902 B1 | 8/2001 | Tedeschi et al. |
| 6,277,138 B1 | 8/2001 | Levinson et al. |
| 6,285,898 B1 | 9/2001 | Ben-Haim |
| 6,290,674 B1 | 9/2001 | Roue et al. |
| 6,290,708 B1 | 9/2001 | Kugel et al. |
| 6,312,407 B1 | 11/2001 | Zadno-Azizi et al. |
| 6,319,251 B1 | 11/2001 | Tu et al. |
| 6,328,727 B1 | 12/2001 | Frazier et al. |
| 6,328,755 B1 | 12/2001 | Marshall |
| 6,342,062 B1 | 1/2002 | Suon et al. |
| 6,346,116 B1 | 2/2002 | Brooks et al. |
| 6,346,895 B1 | 2/2002 | Lee et al. |
| 6,361,545 B1 | 3/2002 | Macoviak et al. |
| 6,364,895 B1 | 4/2002 | Greenhalgh |
| 6,368,338 B1 | 4/2002 | Kónya et al. |
| 6,371,971 B1 | 4/2002 | Tsugita et al. |
| 6,375,670 B1 | 4/2002 | Greenhalgh |
| 6,391,044 B1 | 5/2002 | Yadav et al. |
| 6,398,803 B1 | 6/2002 | Layne et al. |

(56) References Cited

U.S. PATENT DOCUMENTS

| | | |
|---|---|---|
| 6,402,746 B1 | 6/2002 | Whayne et al. |
| 6,402,771 B1 | 6/2002 | Palmer et al. |
| 6,402,779 B1 | 6/2002 | Colone et al. |
| 6,419,669 B1 | 7/2002 | Frazier et al. |
| 6,440,152 B1 | 8/2002 | Gainor et al. |
| 6,443,972 B1 | 9/2002 | Bosma et al. |
| 6,447,530 B1 | 9/2002 | Ostrovsky et al. |
| 6,454,775 B1 | 9/2002 | Demarais et al. |
| 6,458,145 B1 | 10/2002 | Ravenscroft et al. |
| 6,464,712 B1 | 10/2002 | Epstein et al. |
| 6,468,291 B2 | 10/2002 | Bates et al. |
| 6,468,301 B1 | 10/2002 | Amplatz et al. |
| 6,485,501 B1 | 11/2002 | Green |
| 6,488,689 B1 | 12/2002 | Kaplan et al. |
| 6,511,496 B1 | 1/2003 | Huter et al. |
| 6,514,280 B1 | 2/2003 | Gilson |
| 6,517,573 B1 | 2/2003 | Pollock et al. |
| 6,533,782 B2 | 3/2003 | Howell et al. |
| 6,547,760 B1 | 4/2003 | Samson et al. |
| 6,547,815 B2 | 4/2003 | Myers |
| 6,551,303 B1 | 4/2003 | Van Tassel et al. |
| 6,551,344 B2 | 4/2003 | Thill |
| 6,558,401 B1 | 5/2003 | Azizi |
| 6,558,405 B1 | 5/2003 | McInnes |
| 6,558,414 B2 | 5/2003 | Layne |
| 6,562,058 B2 | 5/2003 | Seguin et al. |
| 6,569,184 B2 | 5/2003 | Huter |
| 6,569,214 B2 | 5/2003 | Williams et al. |
| 6,589,214 B2 | 7/2003 | McGuckin et al. |
| 6,589,251 B2 | 7/2003 | Yee et al. |
| 6,599,308 B2 | 7/2003 | Amplatz |
| 6,602,271 B2 | 8/2003 | Adams et al. |
| 6,623,508 B2 | 9/2003 | Shaw et al. |
| 6,641,564 B1 | 11/2003 | Kraus |
| 6,650,923 B1 | 11/2003 | Lesh et al. |
| 6,652,555 B1 | 11/2003 | VanTassel et al. |
| 6,652,556 B1 | 11/2003 | VanTassel et al. |
| 6,666,861 B1 | 12/2003 | Grabek |
| 6,689,150 B1 | 2/2004 | Vantassel et al. |
| 6,699,260 B2 | 3/2004 | Dubrul et al. |
| 6,699,276 B2 | 3/2004 | Sogard et al. |
| 6,702,825 B2 | 3/2004 | Frazier et al. |
| 6,712,836 B1 | 3/2004 | Berg et al. |
| 6,726,701 B2 | 4/2004 | Gilson et al. |
| 6,730,108 B2 | 5/2004 | Van Tassel et al. |
| 6,755,812 B2 | 6/2004 | Peterson et al. |
| 6,827,737 B2 | 12/2004 | Hill et al. |
| 6,837,901 B2 | 1/2005 | Rabkin et al. |
| 6,855,153 B2 | 2/2005 | Saadat |
| 6,911,037 B2 | 6/2005 | Gainor et al. |
| 6,932,838 B2 | 8/2005 | Schwartz et al. |
| 6,942,653 B2 | 9/2005 | Quinn |
| 6,949,113 B2 | 9/2005 | Van Tassel et al. |
| 6,958,061 B2 | 10/2005 | Truckai et al. |
| 6,994,092 B2 | 2/2006 | van der Burg et al. |
| 7,011,671 B2 | 3/2006 | Welch |
| 7,014,645 B2 | 3/2006 | Greene, Jr. et al. |
| 7,037,321 B2 | 5/2006 | Sachdeva et al. |
| 7,044,134 B2 | 5/2006 | Khairkhahan et al. |
| 7,097,651 B2 | 8/2006 | Harrison et al. |
| 7,128,073 B1 | 10/2006 | van der Burg et al. |
| 7,137,953 B2 | 11/2006 | Eigler et al. |
| 7,152,605 B2 | 12/2006 | Khairkhahan et al. |
| 7,169,164 B2 | 1/2007 | Borillo et al. |
| 7,179,275 B2 | 2/2007 | McGuckin, Jr. et al. |
| 7,226,466 B2 | 6/2007 | Opolski |
| 7,303,526 B2 | 12/2007 | Sharkey et al. |
| 7,317,951 B2 | 1/2008 | Schneider et al. |
| 7,323,002 B2 | 1/2008 | Johnson et al. |
| 7,344,505 B2 | 3/2008 | Stofer et al. |
| 7,484,403 B2 | 2/2009 | Baroni et al. |
| 7,597,704 B2 | 10/2009 | Frazier et al. |
| 7,678,123 B2 | 3/2010 | Chanduszko |
| 7,695,425 B2 | 4/2010 | Schweich et al. |
| 7,713,282 B2 | 5/2010 | Frazier et al. |
| 7,722,641 B2 | 5/2010 | van der Burg et al. |
| 7,727,189 B2 | 6/2010 | VanTassel et al. |
| 7,735,493 B2 | 6/2010 | van der Burg et al. |
| 7,780,694 B2 | 8/2010 | Palmer et al. |
| 7,799,049 B2 | 9/2010 | Ostrovsky et al. |
| 7,811,300 B2 | 10/2010 | Feller, III et al. |
| 7,811,314 B2 | 10/2010 | Fierens et al. |
| 7,862,500 B2 | 1/2011 | Khairkhahan et al. |
| 7,927,365 B2 | 4/2011 | Fierens et al. |
| 7,972,359 B2 | 7/2011 | Kreidler |
| 8,025,495 B2 | 9/2011 | Hardert et al. |
| 8,043,329 B2 | 10/2011 | Khairkhahan et al. |
| 8,052,715 B2 | 11/2011 | Quinn et al. |
| 8,062,282 B2 | 11/2011 | Kolb |
| 8,080,032 B2 | 12/2011 | van der Burg et al. |
| 8,097,015 B2 | 1/2012 | Devellian |
| 8,100,938 B2 | 1/2012 | Figulla et al. |
| 8,142,363 B1 | 3/2012 | Eigler et al. |
| 8,221,384 B2 | 7/2012 | Frazier et al. |
| 8,221,445 B2 | 7/2012 | van Tassel et al. |
| 8,287,563 B2 | 10/2012 | Khairkhahan et al. |
| 8,323,309 B2 | 12/2012 | Khairkhahan et al. |
| 8,388,672 B2 | 3/2013 | Khairkhahan et al. |
| 8,491,623 B2 | 7/2013 | Vogel et al. |
| 8,523,897 B2 | 9/2013 | van Der Burg et al. |
| 8,535,343 B2 | 9/2013 | van Der Burg et al. |
| 8,562,509 B2 | 10/2013 | Bates |
| 8,663,273 B2 | 3/2014 | Khairkhahan et al. |
| 8,685,055 B2 | 4/2014 | VanTassel et al. |
| 8,728,117 B2 | 5/2014 | Janardhan et al. |
| 8,758,389 B2 | 6/2014 | Glimsdale |
| 8,828,051 B2 | 9/2014 | Javois et al. |
| 8,834,519 B2 | 9/2014 | van der Burg et al. |
| 8,845,711 B2 | 9/2014 | Miles et al. |
| 9,034,006 B2 | 5/2015 | Quinn et al. |
| 9,132,000 B2 | 9/2015 | VanTassel et al. |
| 9,168,043 B2 | 10/2015 | van Der Burg et al. |
| 9,211,124 B2 | 12/2015 | Campbell et al. |
| 9,295,472 B2 | 3/2016 | Ottma |
| 9,351,716 B2 | 5/2016 | Miles et al. |
| 9,445,895 B2 | 9/2016 | Kreidler |
| 9,554,804 B2 | 1/2017 | Erzbeger |
| 9,554,806 B2 | 1/2017 | Larsen et al. |
| 9,561,037 B2 | 2/2017 | Fogarty et al. |
| 9,561,097 B1 | 2/2017 | Kim et al. |
| 9,592,058 B2 | 3/2017 | Erzbeger et al. |
| 9,597,088 B2 | 3/2017 | Ottma |
| 9,629,636 B2 | 4/2017 | Fogarty et al. |
| 9,730,701 B2 | 8/2017 | Tischler et al. |
| 9,743,932 B2 | 8/2017 | Amplatz et al. |
| 9,750,505 B2 | 9/2017 | Miles et al. |
| 9,763,666 B2 | 9/2017 | Wu et al. |
| 9,795,387 B2 | 10/2017 | Miles et al. |
| 9,808,253 B2 | 11/2017 | Li et al. |
| 9,883,936 B2 | 2/2018 | Sutton et al. |
| 9,913,652 B2 | 3/2018 | Bridgeman et al. |
| 9,943,299 B2 | 4/2018 | Khairkhahan et al. |
| 9,943,315 B2 | 4/2018 | Kaplan et al. |
| 10,071,181 B1 | 9/2018 | Penegor et al. |
| 10,076,335 B2 | 9/2018 | Zaver et al. |
| 10,143,458 B2 | 12/2018 | Kreidler |
| 10,201,337 B2 | 2/2019 | Glimsdale |
| 10,231,737 B2 | 3/2019 | Amplatz et al. |
| 2001/0000797 A1 | 5/2001 | Mazzocchi |
| 2001/0020181 A1 | 9/2001 | Layne |
| 2001/0034537 A1 | 10/2001 | Shaw et al. |
| 2001/0037141 A1 | 11/2001 | Yee et al. |
| 2002/0022860 A1 | 2/2002 | Borillo et al. |
| 2002/0035374 A1 | 3/2002 | Borillo et al. |
| 2002/0045931 A1 | 4/2002 | Sogard et al. |
| 2002/0062133 A1 | 5/2002 | Gilson et al. |
| 2002/0082638 A1 | 6/2002 | Porter et al. |
| 2002/0082675 A1 | 6/2002 | Myers |
| 2002/0099439 A1 | 7/2002 | Schwartz et al. |
| 2002/0111647 A1 | 8/2002 | Khairkhahan et al. |
| 2002/0138094 A1 | 9/2002 | Borillo et al. |
| 2002/0138097 A1 | 9/2002 | Ostrovsky et al. |
| 2002/0169475 A1 | 11/2002 | Gainor et al. |
| 2002/0177855 A1 | 11/2002 | Greene, Jr. et al. |

(56) References Cited

U.S. PATENT DOCUMENTS

| | | |
|---|---|---|
| 2003/0017775 A1 | 1/2003 | Dong et al. |
| 2003/0023262 A1 | 1/2003 | Welch |
| 2003/0023266 A1 | 1/2003 | Borillo et al. |
| 2003/0055345 A1 | 3/2003 | Figler et al. |
| 2003/0057156 A1 | 3/2003 | Peterson et al. |
| 2003/0060871 A1 | 3/2003 | Hill et al. |
| 2003/0120337 A1 | 6/2003 | Van Tassel et al. |
| 2003/0130581 A1 | 7/2003 | Salo et al. |
| 2003/0181942 A1 | 9/2003 | Sutton et al. |
| 2003/0191526 A1 | 10/2003 | Van Tassel et al. |
| 2003/0195555 A1 | 10/2003 | Khairkhahan et al. |
| 2003/0199923 A1 | 10/2003 | Khairkhahan et al. |
| 2003/0204203 A1 | 10/2003 | Khairkhahan et al. |
| 2003/0208214 A1 | 11/2003 | Loshakove et al. |
| 2003/0212432 A1 | 11/2003 | Khairkhahan et al. |
| 2003/0220667 A1 | 11/2003 | van der Burg et al. |
| 2004/0034366 A1 | 2/2004 | van der Burg et al. |
| 2004/0044361 A1 | 3/2004 | Frazier et al. |
| 2004/0049210 A1 | 3/2004 | VanTassel et al. |
| 2004/0093012 A1 | 5/2004 | Cully et al. |
| 2004/0098031 A1 | 5/2004 | van der Burg et al. |
| 2004/0122467 A1 | 6/2004 | VanTassel et al. |
| 2004/0127935 A1 | 7/2004 | VanTassel et al. |
| 2004/0147969 A1* | 7/2004 | Mann ................. A61B 5/02108 607/17 |
| 2004/0158274 A1 | 8/2004 | WasDyke |
| 2004/0186486 A1 | 9/2004 | Roue et al. |
| 2004/0215230 A1 | 10/2004 | Frazier et al. |
| 2004/0220610 A1 | 11/2004 | Kreidler et al. |
| 2004/0220682 A1 | 11/2004 | Levine et al. |
| 2004/0230222 A1 | 11/2004 | van der Burg et al. |
| 2005/0004641 A1 | 1/2005 | Pappu |
| 2005/0004652 A1 | 1/2005 | van der Burg et al. |
| 2005/0015109 A1 | 1/2005 | Lichtenstein |
| 2005/0038470 A1 | 2/2005 | van der Burg et al. |
| 2005/0049573 A1 | 3/2005 | Van Tassel et al. |
| 2005/0070952 A1 | 3/2005 | Devellian |
| 2005/0113861 A1 | 5/2005 | Corcoran et al. |
| 2005/0125020 A1 | 6/2005 | Meade et al. |
| 2005/0177182 A1 | 8/2005 | van der Burg et al. |
| 2005/0203568 A1 | 9/2005 | Burg et al. |
| 2005/0283186 A1 | 12/2005 | Berrada et al. |
| 2005/0288596 A1 | 12/2005 | Figler et al. |
| 2005/0288704 A1 | 12/2005 | Cartier et al. |
| 2006/0015136 A1 | 1/2006 | Besselink |
| 2006/0030877 A1 | 2/2006 | Martinez et al. |
| 2006/0052816 A1 | 3/2006 | Bates et al. |
| 2006/0100658 A1 | 5/2006 | Obana et al. |
| 2006/0155323 A1 | 7/2006 | Porter et al. |
| 2006/0247680 A1 | 11/2006 | Amplatz et al. |
| 2007/0066993 A1 | 3/2007 | Kreidler |
| 2007/0083227 A1 | 4/2007 | van der Burg et al. |
| 2007/0083230 A1 | 4/2007 | Javois |
| 2007/0112380 A1 | 5/2007 | Figulla et al. |
| 2007/0150041 A1 | 6/2007 | Evans et al. |
| 2007/0156123 A1 | 7/2007 | Moll et al. |
| 2007/0162048 A1 | 7/2007 | Quinn et al. |
| 2007/0185471 A1 | 8/2007 | Johnson |
| 2007/0255112 A1 | 11/2007 | Taepke, II et al. |
| 2008/0275536 A1 | 11/2008 | Zarins et al. |
| 2009/0005803 A1 | 1/2009 | Batiste |
| 2009/0062841 A1 | 3/2009 | Amplatz et al. |
| 2009/0099647 A1 | 4/2009 | Glimsdale et al. |
| 2009/0105747 A1 | 4/2009 | Chanduszko et al. |
| 2009/0112249 A1 | 4/2009 | Miles et al. |
| 2009/0254195 A1 | 10/2009 | Khairkhan et al. |
| 2009/0312650 A1 | 12/2009 | Maile et al. |
| 2009/0318948 A1 | 12/2009 | Linder et al. |
| 2010/0004726 A1 | 1/2010 | Hancock et al. |
| 2010/0049238 A1 | 2/2010 | Simpson |
| 2010/0106178 A1 | 4/2010 | Obermiller et al. |
| 2010/0324585 A1 | 12/2010 | Miles et al. |
| 2011/0054515 A1 | 3/2011 | Bridgeman et al. |
| 2011/0082495 A1 | 4/2011 | Ruiz |
| 2011/0098525 A1 | 4/2011 | Kermode et al. |
| 2011/0152698 A1* | 6/2011 | Greenhut ............. A61B 5/0215 600/486 |
| 2011/0218566 A1 | 9/2011 | van der Burg et al. |
| 2011/0301630 A1 | 12/2011 | Hendriksen et al. |
| 2012/0029553 A1 | 2/2012 | Quinn et al. |
| 2012/0035643 A1 | 2/2012 | Khairkhahan et al. |
| 2012/0065662 A1 | 3/2012 | van der Burg et al. |
| 2012/0125619 A1 | 5/2012 | Wood et al. |
| 2012/0172654 A1 | 7/2012 | Bates |
| 2012/0172927 A1 | 7/2012 | Campbell et al. |
| 2012/0239077 A1 | 9/2012 | Zaver et al. |
| 2012/0239083 A1 | 9/2012 | Kreidler |
| 2012/0245619 A1 | 9/2012 | Guest |
| 2012/0271337 A1 | 10/2012 | Figulla et al. |
| 2012/0283585 A1 | 11/2012 | Werneth et al. |
| 2012/0283773 A1 | 11/2012 | Van Tassel et al. |
| 2012/0323267 A1 | 12/2012 | Ren |
| 2013/0006343 A1 | 1/2013 | Kassab et al. |
| 2013/0012982 A1 | 1/2013 | Khairkhahan et al. |
| 2013/0018413 A1 | 1/2013 | Oral et al. |
| 2013/0110154 A1 | 5/2013 | van der Burg et al. |
| 2013/0131717 A1 | 5/2013 | Glimsdale |
| 2013/0165735 A1 | 6/2013 | Khairkhahan et al. |
| 2013/0165801 A1* | 6/2013 | Min ..................... A61B 5/0215 607/119 |
| 2013/0211492 A1 | 8/2013 | Schneider et al. |
| 2013/0296912 A1 | 11/2013 | Ottma |
| 2013/0331884 A1 | 12/2013 | Van der Burg et al. |
| 2013/0338686 A1 | 12/2013 | Ruiz |
| 2014/0005714 A1 | 1/2014 | Quick et al. |
| 2014/0018841 A1 | 1/2014 | Peiffer et al. |
| 2014/0039536 A1 | 2/2014 | Cully et al. |
| 2014/0046360 A1 | 2/2014 | van der Burg et al. |
| 2014/0081314 A1 | 3/2014 | Zaver et al. |
| 2014/0100596 A1 | 4/2014 | Rudman et al. |
| 2014/0142612 A1 | 5/2014 | Li et al. |
| 2014/0148842 A1 | 5/2014 | Khairkhahan et al. |
| 2014/0163605 A1 | 6/2014 | VanTassel et al. |
| 2014/0188157 A1 | 7/2014 | Clark |
| 2014/0214077 A1 | 7/2014 | Glimsdale |
| 2014/0296908 A1 | 10/2014 | Ottma et al. |
| 2014/0303719 A1 | 10/2014 | Cox et al. |
| 2014/0336612 A1 | 11/2014 | Frydlewski et al. |
| 2014/0336699 A1 | 11/2014 | van der Burg et al. |
| 2014/0364941 A1 | 12/2014 | Edmiston et al. |
| 2015/0005810 A1 | 1/2015 | Center et al. |
| 2015/0039021 A1 | 2/2015 | Khairkhahan et al. |
| 2015/0080903 A1 | 3/2015 | Dillard et al. |
| 2015/0196300 A1 | 7/2015 | Tischler et al. |
| 2015/0230909 A1 | 8/2015 | Zaver et al. |
| 2015/0238197 A1 | 8/2015 | Quinn et al. |
| 2015/0305727 A1 | 10/2015 | Karimov et al. |
| 2015/0313604 A1 | 11/2015 | Roue et al. |
| 2015/0313605 A1 | 11/2015 | Griffin |
| 2015/0327979 A1 | 11/2015 | Quinn et al. |
| 2015/0374491 A1 | 12/2015 | Kreidler |
| 2016/0015397 A1 | 1/2016 | Figulla et al. |
| 2016/0051358 A1 | 2/2016 | Sutton et al. |
| 2016/0058539 A1 | 3/2016 | VanTassel et al. |
| 2016/0066922 A1 | 3/2016 | Bridgeman et al. |
| 2016/0106437 A1 | 4/2016 | van der Burg et al. |
| 2016/0192942 A1 | 7/2016 | Strauss et al. |
| 2016/0287259 A1 | 10/2016 | Hanson et al. |
| 2016/0331382 A1 | 11/2016 | Center et al. |
| 2016/0374657 A1 | 12/2016 | Kreidler |
| 2017/0007262 A1 | 1/2017 | Amplatz et al. |
| 2017/0027552 A1 | 2/2017 | Turkington et al. |
| 2017/0042550 A1 | 2/2017 | Chakraborty et al. |
| 2017/0056166 A1 | 3/2017 | Ratz et al. |
| 2017/0065191 A1 | 3/2017 | Jayaraman et al. |
| 2017/0100112 A1 | 4/2017 | van der Burg et al. |
| 2017/0119400 A1 | 5/2017 | Amplatz et al. |
| 2017/0181751 A1 | 6/2017 | Larsen et al. |
| 2017/0340336 A1 | 11/2017 | Osypka |
| 2017/0354421 A1 | 12/2017 | Maguire et al. |
| 2018/0064446 A1 | 3/2018 | Figulla et al. |
| 2018/0070950 A1 | 3/2018 | Zaver et al. |
| 2018/0110468 A1 | 4/2018 | Goldshtein et al. |
| 2018/0140412 A1 | 5/2018 | Sutton et al. |

(56) References Cited

U.S. PATENT DOCUMENTS

| | | | |
|---|---|---|---|
| 2018/0140413 A1 | 5/2018 | Quinn et al. |
| 2018/0186622 A1 | 7/2018 | Mögelin et al. |
| 2018/0250014 A1 | 9/2018 | Melanson et al. |
| 2018/0369594 A1 | 12/2018 | Werneth et al. |
| 2019/0133563 A1 | 5/2019 | Glimsdale |
| 2019/0175185 A1 | 6/2019 | Amplatz et al. |
| 2019/0223883 A1 | 7/2019 | Anderson et al. |
| 2019/0247053 A1 | 8/2019 | Inouye |
| 2019/0336135 A1 | 11/2019 | Inouye et al. |

FOREIGN PATENT DOCUMENTS

| | | | |
|---|---|---|---|
| CN | 104287804 A | 1/2015 |
| CN | 104352261 A | 2/2015 |
| CN | 106859722 A | 6/2017 |
| CN | 10964173 A | 3/2019 |
| DE | 10201004476 A1 | 3/2012 |
| EP | 1523957 A2 | 4/2005 |
| EP | 1595504 A1 | 11/2005 |
| EP | 1463561 B1 | 7/2008 |
| EP | 2074953 A1 | 1/2009 |
| EP | 2481381 A1 | 8/2012 |
| EP | 2928420 A1 | 10/2015 |
| EP | 3072461 A1 | 9/2016 |
| EP | 3372173 A2 | 9/2018 |
| EP | 3398523 A1 | 11/2018 |
| JP | 2003532457 A | 11/2003 |
| JP | 2005324019 A | 11/2005 |
| JP | 2007503286 A | 2/2007 |
| JP | 2007513684 A | 5/2007 |
| JP | 2009160402 A | 7/2009 |
| JP | 2012501793 A | 1/2012 |
| JP | 2016539698 A | 12/2016 |
| WO | 9313712 A1 | 7/1993 |
| WO | 9504132 A1 | 2/1995 |
| WO | 9522359 A1 | 8/1995 |
| WO | 9601591 A1 | 1/1996 |
| WO | 9640356 A1 | 12/1996 |
| WO | 9721402 A1 | 6/1997 |
| WO | 9726939 A1 | 7/1997 |
| WO | 9728749 A1 | 8/1997 |
| WO | 9735522 A1 | 10/1997 |
| WO | 9802100 A1 | 1/1998 |
| WO | 9817187 A1 | 4/1998 |
| WO | 9822026 A1 | 5/1998 |
| WO | 9823322 A1 | 6/1998 |
| WO | 9827868 A1 | 7/1998 |
| WO | 9905977 A1 | 2/1999 |
| WO | 9907289 A1 | 2/1999 |
| WO | 9908607 A1 | 2/1999 |
| WO | 9923976 A1 | 5/1999 |
| WO | 9925252 A1 | 5/1999 |
| WO | 9930640 A1 | 6/1999 |
| WO | 9944510 A1 | 9/1999 |
| WO | 9959479 A1 | 11/1999 |
| WO | 0001308 A1 | 1/2000 |
| WO | 0016705 A1 | 3/2000 |
| WO | 0027292 A1 | 5/2000 |
| WO | 0035352 A1 | 6/2000 |
| WO | 0053120 A1 | 9/2000 |
| WO | 0067669 A1 | 11/2000 |
| WO | 0108743 A1 | 2/2001 |
| WO | 0115629 A1 | 3/2001 |
| WO | 0121247 A1 | 3/2001 |
| WO | 0126726 A1 | 4/2001 |
| WO | 0130266 A1 | 5/2001 |
| WO | 0130267 A1 | 5/2001 |
| WO | 0130268 A1 | 5/2001 |
| WO | 0170119 A1 | 9/2001 |
| WO | 0215793 A2 | 2/2002 |
| WO | 0224106 A2 | 3/2002 |
| WO | 02071977 A2 | 9/2002 |
| WO | 03007825 A1 | 1/2003 |
| WO | 03008030 A2 | 1/2003 |
| WO | 03032818 A1 | 4/2003 |
| WO | 2004012629 A1 | 2/2004 |
| WO | 2007044536 A1 | 4/2007 |
| WO | 2010024801 A1 | 3/2010 |
| WO | 2010081033 A1 | 7/2010 |
| WO | 2013060855 A1 | 5/2013 |
| WO | 2013159065 A1 | 10/2013 |
| WO | 2014011865 A1 | 1/2014 |
| WO | 2014018907 A1 | 1/2014 |
| WO | 2014089129 A1 | 6/2014 |
| WO | 201406239 A1 | 7/2014 |
| WO | 2015080991 A1 | 6/2015 |
| WO | 2015164836 A1 | 10/2015 |
| WO | 2016087145 A1 | 6/2016 |
| WO | 2018017935 A1 | 1/2018 |
| WO | 2018024866 A1 | 2/2018 |
| WO | 2018187732 A1 | 10/2018 |
| WO | 2019084358 A1 | 5/2019 |

OTHER PUBLICATIONS

International Search Report and Written Opinion dated Feb. 15, 2000 for International Application No. PCT/US99/26325.
International Search Report dated May 20, 2003 for International Application No. PCT/US02/33808.
Written Opinion dated Nov. 17, 2003 for International Application No. PCT/US/02/33808.
International Search Report and Written Opinion dated Aug. 21, 2018 for International Application No. PCT/US2018/029684.
Cragg et al., "A New Percutaneous Vena Cava Filter," American Journal of Radiology, Sep. 1983, pp. 601-604, vol. 141.
Cragg et al, "Nonsurgical Placement of Arterial Endoprostheses: A New Technique Using Nitinol Wire," Radiology, Apr. 1983, pp. 261-263, vol. 147, No. 1.
Lock et al., "Transcatheter Closure of Atrial Septal Defects." Circulation, May 1989, pp. 1091-1099, vol. 79, No. 5.
Lock et al., "Transcatheter Umbrella Closure of Congenital Heart Defects," Circulation, Mar. 1987, pp. 593-599, vol. 75, No. 3.
Rashkind et al., "Nonsurgical closure of patent ductus arteriosus: clinical application of the Rashkind PDA Occluder System," Circulation, Mar. 1987, pp. 583-592, vol. 75, No. 3.
Rosengart et al., "Percutaneous and Minimally Invasive Valve Procedures," Circulation, Apr. 1, 2008, pp. 1750-1767, vol. 117.
Ruttenberg, "Nonsurgical Therapy of Cardiac Disorders," Pediatric Consult, 1986, Pages not numbered, vol. 5, No. 2.
Sugita et al., "Nonsurgical Implantations of a Vascular Ring Prosthesis Using Thermal Shape Memory Ti/Ni Alloy (Nitinol Wire)," Trans. Am. Soc. Artif. Intern. Organs, 1986, pp. 30-34, vol. XXXII.
Wessel et al., "Outpatient Closure of the Patent Ductus Arteriousus," Circulation, 1988, pp. 1068-1071, vol. 77, No. 5.
Tung et al., U.S. Appl. No. 61/559,941, filed Nov. 15, 2011.
Yue Yu et al., U.S. Appl. No. 61/557,880, filed Dec. 20, 2011.
Cline, "File: Fish hooks.jpg," Wikipedia foundation , Inc., San Francisco, CA, Jun. 2007; p. 1 of 4; available online at http://en.wikipedia.org/wiki/File:Fish_hooks.jpg; last accessed Oct. 5, 2012.
International Search Report and Written Opinion dated Apr. 22, 2014 for International Application No. PCT/US2013/078454.
Aryana et al., "Incomplete Closure of the Left Atrial Appendage: Implication and Management." Curr Cardiol Rep., 18(9):82, 2016.
Delurgio, "Device-Associated Thrombus and Peri-Device Leak Following Left Atrial Appendage Closure with the Amplatzer Cardiac Plug." JACC: Cardiovascular Interventions, 10(4): 400-402, 2017.
University of Minnesota. Atlas of Human Cardiac Anatomy, Left Atrium. Retrieved from http://www.vhlab.umn.edu/atlas/left-atrium/left-atrial-appendage/index.shtml. Accessed 2017. Downloaded 2019.
Saw et al., "Incidence and Clinical Impact of Device-Associated Thrombus and Peri-Device Leak following Left Atrial Appendage Closure with the Amplatzer Cardiac Plug." JACC: Cardiovascular Intervention. 10(4): 391-399, 2017.
Romero et al., "Left Atrial Appendage Closure Devices," Clinical Medicine Insights: Cardiology, vol. 8, pp. 45-52, 2014.
Invitation To Pay Additional Fees And, Where Applicable, Protest Fee, mailed Oct. 13, 2016.

(56) References Cited

OTHER PUBLICATIONS

International Search Report and Written Opinion dated Oct. 14, 2019 for International Application No. PCT/US2019/047452.
International Search Report and Written Opinion dated Oct. 27, 2017 for International Application No. PCT/US2017/048150.
International Search Report and Written Opinion dated Jan. 21, 2019 for International Application No. PCT/US2018/051953.
International Search Report and Written Opinion dated Oct. 13, 2016 for International Application No. PCT/US2016/043363.
International Search Report and Written Opinion dated Mar. 17, 2020, for International Application No. PCT/US2019/065243.
International Search Report and Written Opinion dated Sep. 9, 2019 for International Application No. PCT/US2019/033698.
Blackshear et al; "Appendage Obliteration to Reduce Stroke in Cardiac Surgical Patients with Atrial Fibrillation", Ann. Thoracic Surgery, pp. 755-759, 1996.
Lindsay, "Obliteration of the Left Atrial Appendage: A Concept Worth Testing", Ann. Thoracic Surgery, 1996.
Invitation To Pay Additional Fees dated Feb. 22, 2019 for International Application No. PCT/US2018/066163.
International Search Report and Written Opinion dated Oct. 23, 2020 for International Application No. PCT/US2020/042192.
International Search Report and Written Opinion dated Mar. 24, 2022 for International Application No. PCT/US2021/060990.
International Search Report and Written Opinion dated Oct. 13, 2020 for International Application No. PCT/US2020/048437.
International Search Report and Written Opinion dated Jul. 15, 2021 for International Application No. PCT/US2021/023687.
10 Viscoelasticity Document, 60 pages, 2021.
10.2 Examples and Applications of Viscoelastic Materials, 3 pages, 2021.
Boutry et al; "Fully Biodegradable Pressure Sensor, Viscoelastic Behavior of PGS Dielectric Elastomer upon Degradation", IEEE, 4 pages, Authorized Licensed limited to Boston Scientific Corporation. Downloaded on Nov. 30, 2020 from IEEE Xplore.
Hwang et al; "Unveiling Viscoelastic Response of Capacitive-Type Pressure Sensor by Controlling Cross-Linking Density and Surface Structure of Elastomer," ACS Appl. Polym. Mater. 2,6, pp. 2190-2198, 2020.
Tsai et al; "On-Chip Pressure Sensor using Single-Layer Concentric Chambers," Biomicrofluidics, 10, 11 pages, AIP Publishing, 2016.
Viscoelasticity, Wikipedia, 2020. https://wikipedia.org/wiki/Viscoelasticity.

\* cited by examiner

IMPLANTABLE PASSIVE MEAN PRESSURE SENSOR

CROSS REFERENCE TO RELATED APPLICATIONS

This application claims the benefit of U.S. Provisional Patent Application Ser. No. 63/119,337 filed on Nov. 30, 2020, the disclosure of which is incorporated herein by reference.

TECHNICAL FIELD

The present disclosure pertains to pressure sensors. More particularly, the present disclosure pertains to implantable pressure sensors that can provide a mean pressure indication.

BACKGROUND

A variety of pressure sensors have been developed for measuring a variety of different pressures, including blood pressure. Some pressure sensors may be implanted in the body in order to provide blood pressure values. Because they are implanted, there can be issues with being able to provide power to the pressure sensor over time. Moreover, while pressure sensors can provide an instantaneous indication of pressure, they typically are not configured to provide an indication of mean pressure over time. There is an ongoing need for a pressure sensor that can provide an indication of mean pressure over time, particularly without requiring ongoing electrical energy in order to maintain a measurement of mean pressure over time.

SUMMARY

This disclosure pertains to pressure sensors that can provide an indication of mean pressure over time, even without ongoing electrical energy to maintain the indication of mean pressure over time. As an example, an implantable pressure sensor includes a housing and a sensing component that is housed by the housing and exposed to an external pressure that is exterior to the housing. In response to the external pressure, the sensing component is configured to undergo a physical transformation that is representative of a mean pressure of the external pressure over a period of time of at least one minute. The pressure sensor includes circuitry that is operatively coupled to the sensing component and that is responsive to the physical transformation of the sensing component to produce a mean pressure signal that is representative of the mean pressure of the external pressure over the period of time.

Alternatively or additionally, the circuitry may be configured to repeatedly receive an energy transfer from a remote source, and in response, transmit the mean pressure signal back to the remote source.

Alternatively or additionally, the sensing component may undergo and maintain the physical transformation that is representative of the mean pressure of the external pressure over the period of time without the application of electrical power.

Alternatively or additionally, the physical transformation of the sensing component may have a time constant of at least one hour.

Alternatively or additionally, the physical transformation of the sensing component may have a time constant of at least twelve hours.

Alternatively or additionally, the physical transformation of the sensing component may have a time constant of at least 1 day.

Alternatively or additionally, the housing may be adapted for being disposed within a patient's heart, bladder, brain, spinal column, eye, joint or vascular system.

Alternatively or additionally, the sensing component may include a first plate exposed to the external pressure exterior to the housing and configured to move in response to pressure changes within the external pressure, a second plate spaced apart from the first plate and disposed within the housing, and a viscoelastic material disposed between the first plate and the second plate.

Alternatively or additionally, the viscoelastic material may include a non-conductive material, and the mean pressure signal may be representative of a capacitance between the first plate and the second plate.

Alternatively or additionally, the viscoelastic material may include an electrically conductive material, and the mean pressure signal may be an indication of a resistance between the first plate and the second plate.

Alternatively or additionally, the first plate may be electrically conductive and the second plate may be electrically conductive.

Alternatively or additionally, the sensing component may include a hydraulic sensing component.

Alternatively or additionally, the hydraulic sensing component may include a hydraulic chamber exposed to the external pressure, a first fluid disposed within the hydraulic chamber, a pressure chamber, a second fluid disposed within the pressure chamber, and a barrier disposed between the first fluid and the second fluid. Pressure changes in the hydraulic chamber relative to a pressure within the pressure chamber may cause movement of the barrier.

Alternatively or additionally, the barrier may include a low flow valve with a high permeability material.

As another example, an implantable pressure sensor is configured to provide a signal providing an indication of a mean pressure value over a period of time. The implantable pressure sensor includes a housing configured to be implanted in a patient and a sensing component disposed within the housing yet exposed to an environment exterior to the housing. The sensing component is configured to maintain a mean pressure measurement providing an indication of a mean pressure within the environment exterior to the housing over a period of time without electrical energy.

Alternatively or additionally, the sensing component may include a viscoelastic material having a time constant of at least one hour.

As another example, a left atrial appendage closure device is adapted to fit within a patient's left atrial appendage in order to substantially close off the patient's left atrial appendage. The left atrial appendage closure device includes an expandable framework. A sensing component is exposed to a left atrium pressure within the left atrium of the patient's heart once the left atrial appendage closure device is implanted, wherein in response to the left atrium pressure, the sensing component is configured to undergo a physical transformation that is representative of a mean pressure of the left atrium pressure over a period of time of at least 1 minute. Circuitry is operatively coupled to the sensing component and is responsive to the physical transformation of the sensing component to produce a mean pressure signal that is representative of the mean pressure of the left atrium pressure over the period of time.

Alternatively or additionally, the sensing component may include a viscoelastic material with a time constant of at least 10 minutes that, in response to the left atrium pressure, viscoelastically deforms in a manner that represent the mean pressure of the left atrium pressure over the period of time.

Alternatively or additionally, the sensing component may include a hydraulic system including a low flow valve, wherein in response to a positive change in the left atrium pressure, the sensing component moves fluid through the low flow valve under a hydraulic resistance in a first direction subject to a time constant of the sensing component defined at least in part by the low flow valve.

Alternatively or additionally, in response to a negative change in the left atrium pressure, the sensing component may move fluid through the low flow valve in a second direction opposite to the first direction subject to the time constant of the sensing component.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
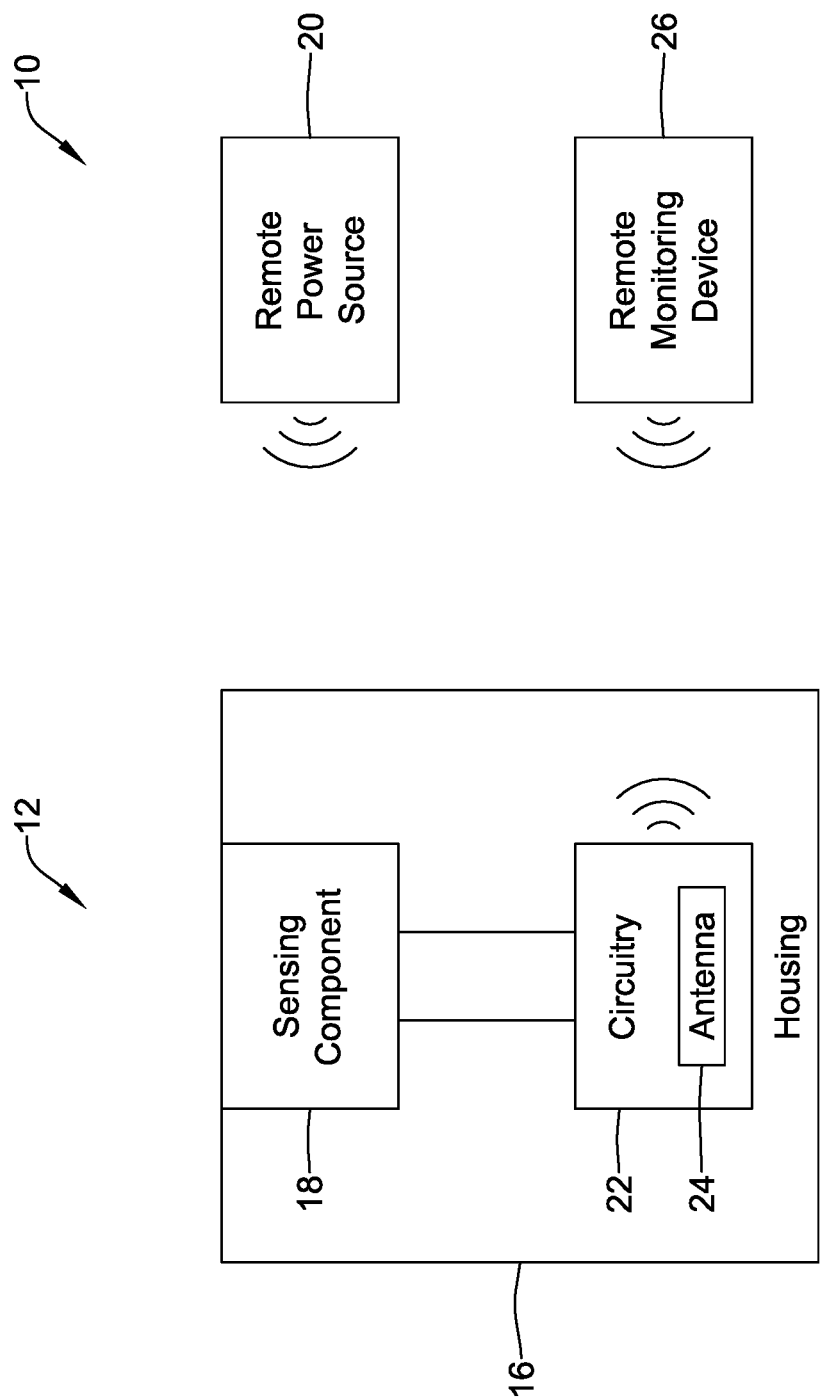
FIG. 1 is a schematic block diagram of an illustrative pressure sensing system.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

FIG. 1 is a schematic block diagram of an illustrative pressure sensing system 10. The pressure sensing system 10 includes a pressure sensor 12 and a remote energy source 20. The pressure sensor 12 may be configured to be implanted within a patient's body. In some cases, the pressure sensor 12 may be configured to be implanted at a location in which the pressure sensor 12 may be exposed to the patient's blood, such as within the patient's vasculature. For example, the pressure sensor 12 may be configured to be implanted within a chamber of the patient's heart. In other cases, the pressure sensor 12 may be configured to be implanted within a patient's bladder, artery, vein, brain, spinal column, eye, joint or other location, for example.

The illustrative pressure sensor 12 includes a housing 16 that is configured to be implanted at a desired location within the patient. While the pressure sensor 12 is described herein as being deployed as an implantable device, intended for use in the human body, it will be appreciated that the pressure sensor 12 may be applied to other applications as well. When intended for use in the human body, the housing 16 may be formed of any suitable biocompatible material, such as a biocompatible polymeric material or a biocompatible metallic material. In some cases, the housing 16 may be formed of a material that is not biocompatible, but may have a biocompatible film or coating covering an exterior of the housing 16.

The pressure sensor 12 may be considered as being configured to provide an indication of a mean pressure, or an average pressure value over time. The mean pressure may be rolling mean pressure taken over a predetermined time horizon. That is, rather than an instantaneous pressure sensor that immediately reports a currently detected pressure, the pressure sensor 12 creates and maintains a mean pressure measurement that is not overly influenced by transient spikes in pressure. For example, a person's blood pressure may spike while they are climbing stairs, or otherwise exerting themselves. An instantaneous blood pressure measurement, especially when taken only at certain time intervals, may not provide an accurate picture of the person's overall cardiovascular health. In contrast, a mean blood pressure measurement may do a better job of ignoring short term pressure spikes to more accurately represent an overall blood pressure trend.

The illustrative pressure sensor 12 includes a sensing component 18. The sensing component 18 may be configured to create and maintain an indication of mean pressure that represents a mean pressure of the environment outside of the housing 16 over time. To that end, the housing 16 may be configured to allow the sensing component 18 or at least a portion thereof to be exposed to the environment outside of the housing 16. In some cases, the sensing component 18 may include a viscoelastic material. A viscoelastic material is a material for which the relationship between stress and strain depends on time, and that includes properties of both viscous and elastic materials. Viscosity is a measure of a fluid's resistance to flow while elasticity is a measure of a material's ability to return to its original shape after application of a force. Sorbothane®, which is a highly damped viscoelastic polymeric solid that flows like a liquid under load is one example viscoelastic material. Sorbothane® is a thermoset, polyether-based, polyurethane material. Memory foam is another example viscoelastic material. Other example viscoelastic materials include some polymers, semi-crystalline polymers, biopolymers, neoprene, and bitumen materials. These materials can be tailored to have a desired time constant to match the desired application.

Rather than using a viscoelastic material, the sensing component 18 may be implemented as a hydraulic system that can track a mean or rolling average of pressure over time. Other systems may also be used. In any event, the sensing component 18 may be considered as being configured to maintain an indication of mean pressure over time without needing any source of electricity to create and maintain the indication of mean pressure. As a result, the pressure sensor 12 does not need any on-board source of power, such as a battery. Rather, the pressure sensor 12 may be configured to periodically receive power transmitted from a remote power source 20. In order for the pressure sensor 12 to be able to receive and utilize the power transmitted from the remote power source 20, the pressure sensor 12 includes circuitry 22 that is operably coupled to the sensing component 18.

The illustrative circuitry 22 includes an antenna 24 that is configured to receive electrical energy from the remote power source 20. The circuitry 22 is configured to convert the electrical energy into an appropriate form, if appropriate, and to use the energy to solicit a signal from the sensing component 18. The circuitry 22 then transmits the signal that provides an indication of the mean pressure measured over time by the sensing component 18 to a remote monitoring device 26. In some cases, a single antenna 24 is able to both receive electrical energy transmitted by the remote power source 20 and to communicate with the remote monitoring device 26. In some instances, the antenna 24 may instead represent a first antenna that is configured to receive electrical energy transmitted by the remote power source 20 and a second antenna that is configured to transmit a signal to the remote monitoring device 26. While the remote power source 20 and the remote monitoring device 26 are illustrated as being separate devices, it will be appreciated that in some cases the remote power source 20 and the remote monitoring device 26 may be incorporated into a single hand-held apparatus.

It should be noted that the electrical energy provided to the pressure sensor 12 from the remote power source 20 is not used to create or maintain an indication of a mean pressure measurement over time. Rather, the indication of the mean pressure measurement over time is created and maintained over time by the sensing component 18 without need for ongoing electrical energy. In this example, the electrical energy provided by the remote power source 20 is only used to query the sensing component 18 for an indication of the mean pressure measurement over time and to transmit a signal representing the indication of the mean pressure measurement over time to the remote monitoring device 26.

In some cases, the sensing component 18 may be considered as having being configured to undergo a physical transformation in response to being exposed to an external pressure outside of the housing 16. The physical transformation may be considered as being representative of a mean pressure of the external pressure over a period of at least one minute. Brief spikes in pressure may be largely ignored. The physical transformation of the sensing component 18 may be considered as having a time constant of at least one hour. The physical transformation of the sensing component 18 may be considered as having a time constant of at least twelve hours. The physical transformation of the sensing component 18 may be considered as having a time constant of at least one day. The time constant here represents the speed at which the sensing component 18 can respond to a change in input pressure, defined here as the time for the mean pressure reported by the sensing component 18 to vary by a factor of $1-1/e$ (approximately 0.6321) in response to a step change in input pressure. That is, for a time constant of one day, when the input pressure P is halved to P/2 at time "t" and is maintained at P/2 for a day, the sensing component 18 would report a mean pressure of $P-(P/2*(1-1/e)) \approx 0.68P$ after one day. This is just an example.

In some cases, a time constant for increased pressure (e.g. a compression time constant) may be configured to be about equal to a time constant for decreased pressure (e.g. expansion time constant) to facilitate the measurement of a mean pressure measurement. In some cases, the time constant for increased pressure and the time constant for decreased pressure may not be equal. For example, there may be a desire to bias the measurement towards higher or lower pressures, or when both time constants are adjusted to account for biological effects (e.g. tissue encapsulation).

In some cases, the signal provided by the circuitry 22, which is representative of the mean pressure measurement provided by the sensing component 18, may be corrected for sensor hysteresis. This correction may occur within the remote monitoring device 26 in order to reduce the computational requirements for the circuitry 22, although in some cases the circuitry 22 may itself correct for sensor hysteresis. In some instances, a second or additional pressure sensor(s) (not illustrated) may also be implanted within a patient in order to provide an instantaneous measurement when desired, in addition to the mean pressure measurement provided by the pressure sensor 12. The second or additional pressure sensor(s) may be part of the pressure sensor 12 and operatively coupled to the circuitry 22. Alternatively, the additional pressure sensor(s) may be separately housed. The additional pressure sensor(s) may be used to calibrate the pressure sensor 12. Alternatively, the pressure sensor 12 may be used to calibrate the instantaneous pressure sensor. It will be appreciated that the pressure sensor 12 (and any additional pressure sensors) may be configured to operate within the range of pressures that are encountered within a vessel or chamber within the human body. For example, the expected absolute pressure range within the left atrium is 450 to 950 millimeters (mm) Hg. The expected gauge pressure within the left atrium is 2 to 90 mm Hg.

Figure 2:
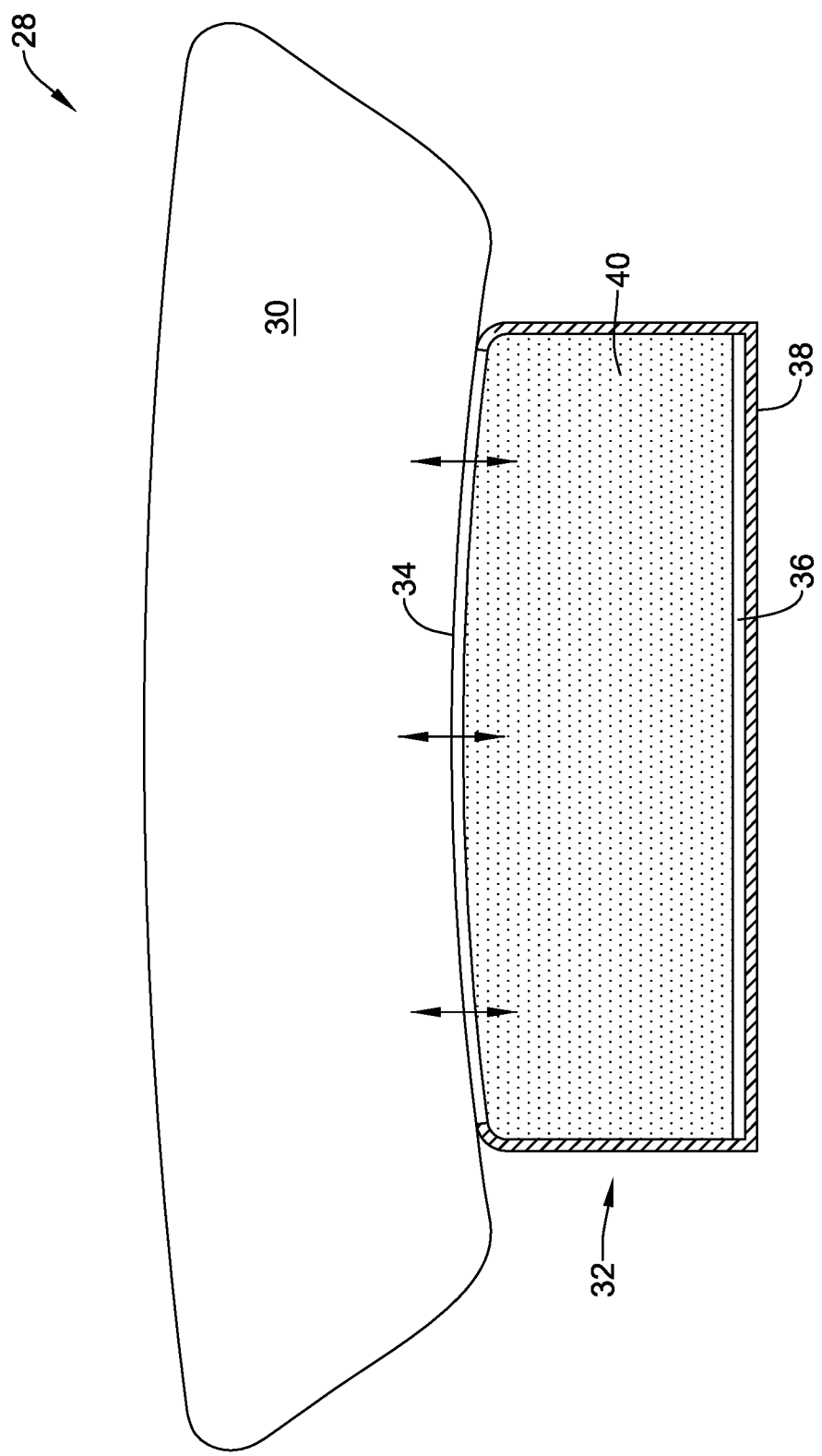
FIG. 2 is a schematic diagram of an illustrative pressure sensor.

FIG. 2 is a schematic diagram of an illustrative pressure sensor 28 that is exposed to an environment 30 having a variable pressure. The pressure sensor 28 may be considered as an example of the pressure sensor 12. The environment 30 may represent part of the patient's vasculature, including their heart, or the patient's bladder or other cavity. The illustrative pressure sensor 28 includes a chamber 32 that is formed between a first plate 34 and a second plate 36. A housing 38, which may be considered as illustrative of the housing 16 shown in FIG. 1, may provide sides and a bottom to the chamber 32. The first plate 34 is positioned such that changes in pressure within the environment 30 may cause the first plate 34 to flex downward (in the illustrated orientation) when the external pressure within the environment 30 increases, and may cause the first plate 34 to flex upward (in the illustrated orientation) when the external pressure within the environment 30 decreases. In this example, the chamber 32 is filled with a viscoelastic material 40.

The first plate 34 and the second plate 36 may be considered as being electrically conductive. In some cases, when the viscoelastic material 40 is not electrically conductive, the physical transformations that have occurred over time to the viscoelastic material 40 may be indicated by detecting a capacitance between the first plate 34 and the second plate 36. In other cases, when the viscoelastic material 40 is electrically conductive, the physical transformations that have occurred over time to the viscoelastic material 40 may be indicated by detecting a resistance between the first plate 34 and the second plate 36. These are just examples.

Figure 3:
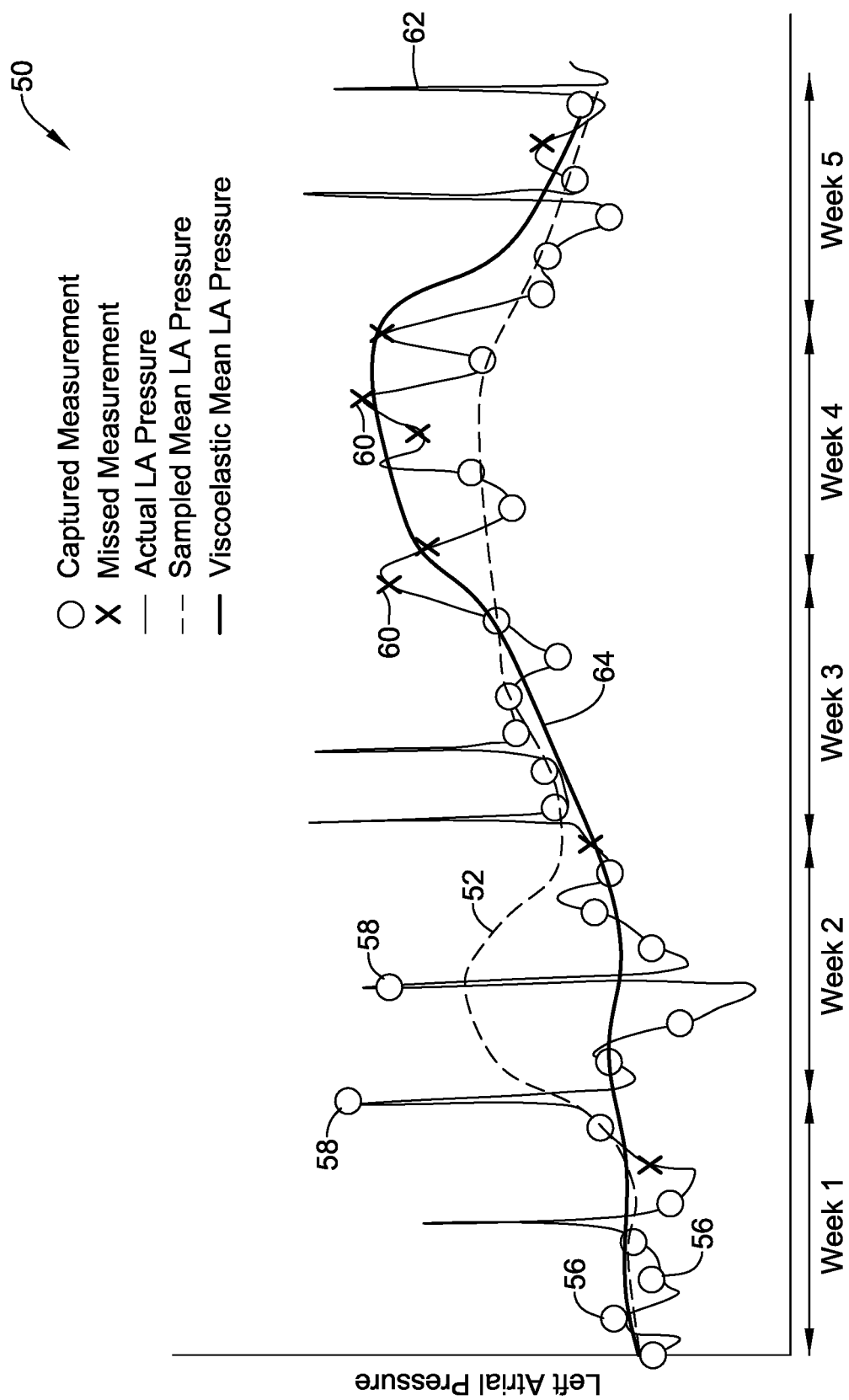
FIG. 3 is a graphical representation of mean pressure data.

FIG. 3 is a graphical representation 50 of how a viscoelastic material may be used to track a mean pressure measurement over time. This particular example tracks left atrial pressure over a time period of five weeks, with the left atrial pressure indicated on the vertical axis while time is indicated on the horizontal axis. This pressure data is not actual pressure data taken from a patient, but rather has been generated to illustrative how a mean pressure measurement over time is able to ignore transient spikes and missed measurements. While this example is specific to use of a viscoelastic material as part of the sensing component 18, it will be appreciated that the lessons taught by this example are equally applicable to other types of the sensing component 18, such as a hydraulic or other system.

A graphed line 52 shows a mean left atrial pressure as determined by periodic instantaneous measurements 56. In some cases, the graphed line 52 indicates that the mean left atrial pressure as determined by periodic instantaneous measurements 56 can be skewed if the instantaneous measurements are taken at a bad time (e.g. at a short term peak). For example, several periodic instantaneous measurements 58 show left atrial pressure values that are high due to a condition that interferes with the desired mean pressure measurement, such as when an instantaneous measurement was taken while the person was exercising. The graphed line 52 also shows that the mean left atrial pressure as determined by periodic instantaneous measurements may be skewed if instantaneous measurements are missing, such as the missed samples 60. A graphed line 62 provides a representation of the patient's actual left atrial pressure. It can be seen that the graphed line 62 passes through each of the periodic instantaneous measurements 56, the badly timed instantaneous measurements 58 and the missed instantaneous measurements 60. It can be seen that the actual pressure can periodically spike.

A graphed line 64 provides a representation of the mean left atrial pressure as determined using a viscoelastic material. It can be seen that the graphed line 64 overall tracks the actual left atrial pressure as indicated by the graphed line 62, and the graphed line 64 is not influenced by the poorly timed instantaneous measurements 58 or by the missed instantaneous measurements 60. This illustrates how the mean pressure measurement may be used as a reliable indication of blood pressure performance without requiring frequent instantaneous measurements. This also illustrates how a viscoelastic material may be used to provide an indication of mean pressure over time in a manner that does not require electrical energy to either create or maintain the indication of mean pressure over time.

Figure 4:
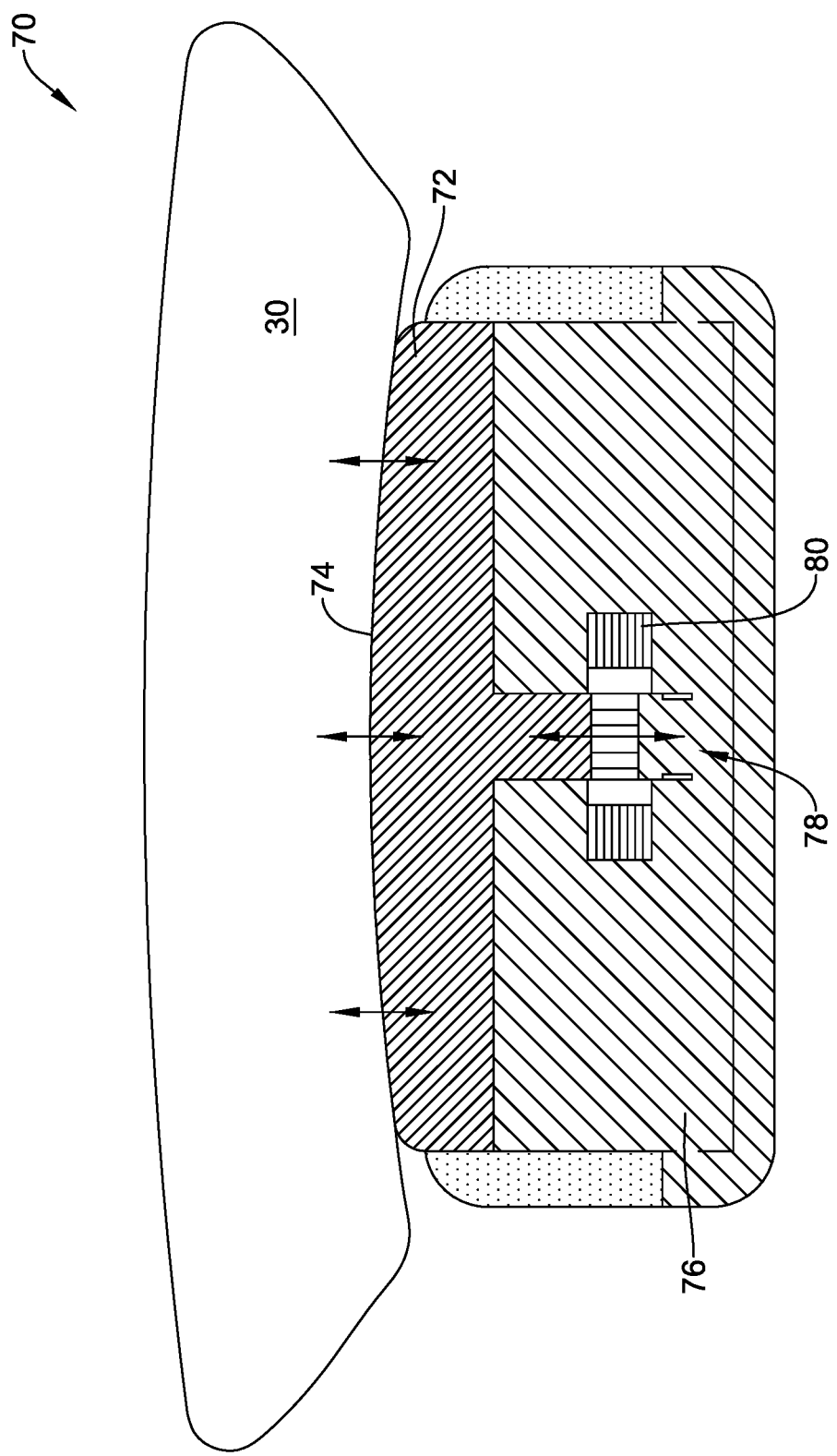
FIG. 4 is a schematic diagram of an illustrative pressure sensor.

FIG. 4 is a schematic diagram of an illustrative pressure sensor 70 that is exposed to an environment 30 having a variable pressure. The pressure sensor 70 may be considered as an example of the pressure sensor 12, and may operate hydraulically. The pressure sensor 70 includes a hydraulic chamber 72 that is exposed to the external pressure within the environment 30. The hydraulic chamber 72 includes a chamber wall 74 that is configured to bend and flex in response to relative pressure differences between the environment 30 and the hydraulic chamber 72. The hydraulic chamber 72 includes a first fluid. The pressure sensor 70 includes a pressure chamber 76 that includes a second fluid. The second fluid may be the same as the first fluid. In some cases, the first fluid may be a liquid. In some cases, the second fluid may be a liquid. A barrier 78 is fluidly coupled between the hydraulic chamber 72 and the pressure chamber 76. The hydraulic chamber 72 may be considered as acting as a movement multiplier, such that relatively small pressure differences between the environment 30 and the hydraulic chamber 72 result in detectable movement of the barrier 78.

In the example shown, the barrier 78 includes a low flow valve with a high permeability material. As the external pressure within the environment 30 changes, the barrier 78 fluidly disposed between the hydraulic chamber 72 and the pressure chamber 76 moves in response thereto. Also, a maintained external pressure causes some of the fluid to slowly flow through the low flow valve, moving between the hydraulic chamber 72 and the pressure chamber 76. The rate of flow through the low flow valve of the barrier 78 may be chosen to set the time constant of the pressure sensor 70. This physical transformation of the barrier 78 and movement of the fluid between the hydraulic chamber 72 and the pressure chamber 76 is representative of the mean external pressure. To read the mean pressure value, a coil 80 may be coupled with the barrier 78. As the barrier 78 moves in response to pressure changes, the inductance of the coil 80 will change. Accordingly, measuring the inductance of the coil 80 may provide an indication of the mean pressure measurement when the hydraulic chamber 72, the pressure chamber 76 and the fluids therein are non-conductive.

Figure 4B:
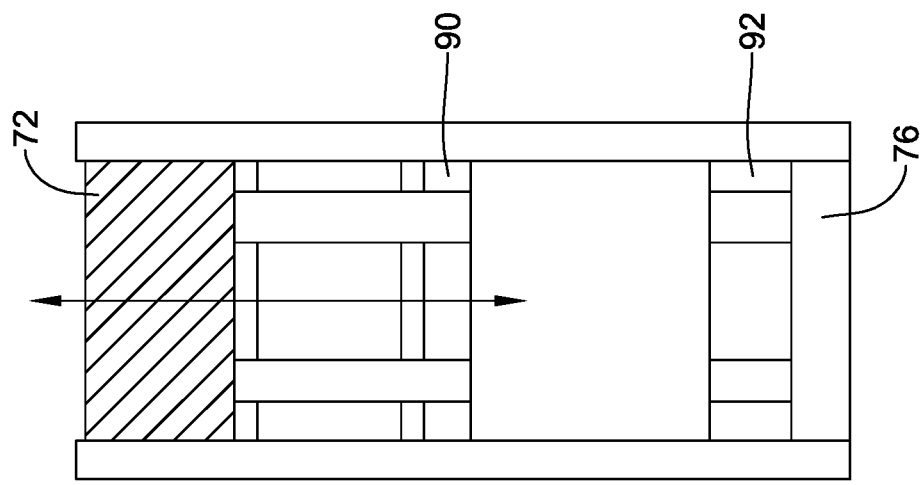
FIG. 4B is a schematic diagram of a portion of an illustrative pressure sensor.
Figure 4A:
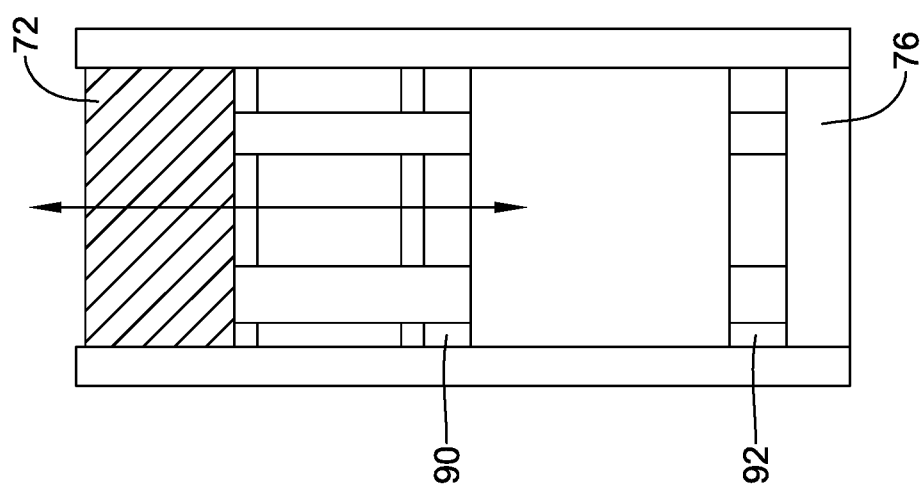
FIG. 4A is a schematic diagram of a portion of an illustrative pressure sensor.

FIG. 4A illustrates a version of the pressure sensor 70 in which capacitance is used to provide an indication of mean pressure. In FIG. 4A, a first plate 90 and a second plate 92 are conductive and function as the barrier 78 (FIG. 4) with a low flow valve. In some cases, the first plate 90 moves in response to changes in mean pressure while the second plate 92 does not. As the distance between the first plate 90 and the second plate 92 varies in accordance with pressure changes, the capacitance between the first plate 90 and the second plate 92 may be used as an indication of the mean pressure measurement. In FIG. 4A, the first and second fluids are electrically non-conductive or substantially electrically non-conductive. In this, substantially electrically non-conductive means that the fluids are not sufficiently electrically conductive to interfere with a capacitance measurement. In FIG. 4B, electrically conductive liquids are used, and changes in resistance between the first plate 90 and the second plate 92 may be used as an indication of the mean pressure measurement.

Figure 5:
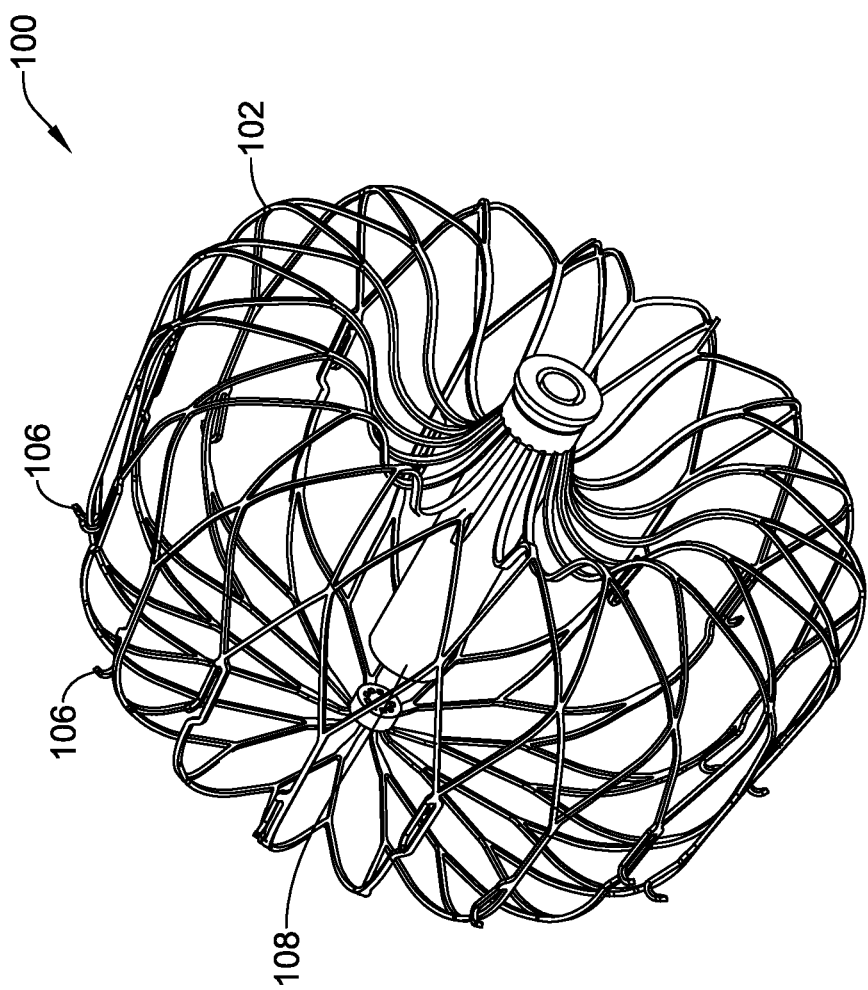
FIG. 5 is a perspective view of an illustrative left atrial appendage closure device.
Figure 6:
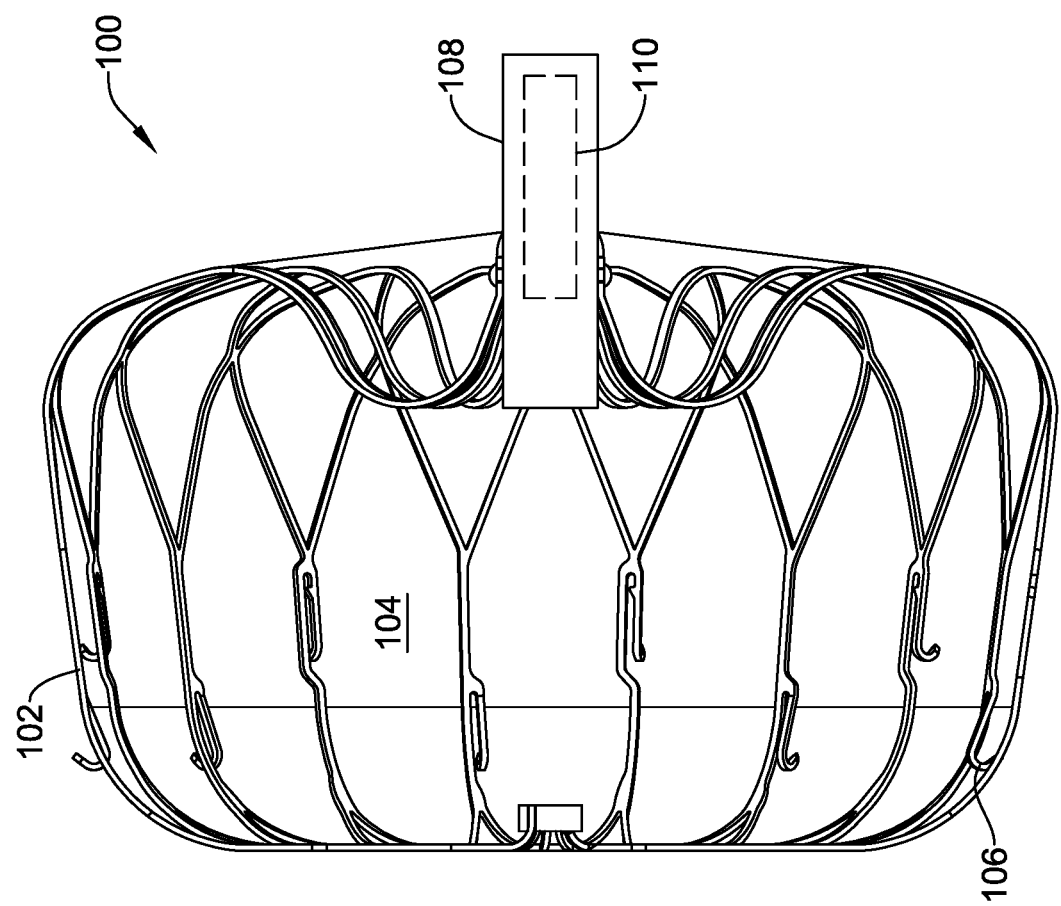
FIG. 6 is a side view of the illustrative left atrial appendage closure device of FIG. 5.

FIG. 5 is a perspective view of an illustrative left atrial appendage closure device 100 while FIG. 6 is a side view thereof showing the left atrial appendage closure device 100 including an occlusive element 104. The left atrial appendage closure device 100 includes an expandable framework 102 that is configured to convert between a collapsed configuration (for delivery) and an expanded configuration, as shown. In some instances, the expandable framework may be compliant and may substantially conform to and/or be in sealing engagement with the shape and/or geometry of a lateral wall and/or an ostium of a left atrial appendage in the expanded configuration. The left atrial appendage closure device 100 may expand to a size, extent, or shape less than or different from a maximum unconstrained extent, as determined by the surrounding tissue and/or lateral wall of the left atrial appendage. Reducing a thickness of various elements of the expandable framework 102 may increase the flexibility and compliance of the expandable framework 102 and/or the left atrial appendage closure device 100, thereby permitting the expandable framework 102 and/or the left atrial appendage closure device 100 to conform to the tissue around it, rather than forcing the tissue to conform to the expandable framework 102 and/or the left atrial appendage closure device 100.

In some cases, as shown in FIG. 6, the left atrial appendage closure device 100 may optionally include an occlusive element 104 (e.g., a mesh, a fabric, a membrane, and/or other surface treatment) disposed on, disposed over, disposed about, or covering at least a portion of the expandable framework 102. In some embodiments, the occlusive element 104 may be disposed on, disposed over, disposed about or cover at least a portion of an outer (or outwardly facing) surface of the expandable framework 102.

In some embodiments, the expandable framework 102 may include a plurality of anchor members 106 disposed about a periphery of the expandable framework 102 in the expanded configuration. The plurality of anchor members 106 may extend radially outward from the expandable framework 102. In some embodiments, at least some of the plurality of anchor members 106 may each have and/or include a body portion, a tip portion, and a barb projecting circumferentially therefrom. In some embodiments, some and/or each of the plurality of anchor members 106 have at least one barb projecting circumferentially therefrom. The plurality of anchor members 106 may provide an anchoring mechanism to aid in retaining the left atrial appendage closure device 100 at a target site within a patient's anatomy (i.e., the left atrial appendage, for example) in the expanded configuration. However, the barb(s) may be configured, positioned, and/or arranged such that engagement of the barb(s) with surrounding tissue at the target site is minimized. For example, the barb(s) may not puncture, pierce, and/or extend into the surrounding tissue in the expanded configuration. Additionally, in some embodiments, the plurality of anchor members 106 may provide an attachment mechanism for securing the occlusive element 104 to the expandable framework 102.

The left atrial appendage closure device 100 may include a central post 108 from which at least some components of the expandable framework 102 may extend. In some instances, as best seen in FIG. 6, the central post 108 may include a pressure sensor 110 disposed within the central post 108. In this, the central post 108 may function at least in part as a housing for the pressure sensor 110. While shown schematically, the pressure sensor 110 may represent the pressure sensor 12 shown in FIG. 1. The pressure sensor 110 may represent the pressure sensor 28 shown in FIG. 2. The pressure sensor 110 may represent the pressure sensor 70 shown in FIG. 4. It will be appreciated that by placing the pressure sensor 110 within the central post 108, or securing the pressure sensor 110 to any other portion of the left atrial appendage closure device 100, it is possible to obtain a mean left atrial pressure measurement over time of the left atrium. In some cases, the pressure sensor 110 may extend a substantial portion of the length of the central post 108, but this is not required.

Because endothelization makes removal of the left atrial appendage closure device 100 difficult, having a pressure sensor such as the pressure sensor 110 that can provide an indication of mean left atrial blood pressure over time, without requiring any onboard power supply, means that there are no concerns with battery life, for example. A doctor or other medical professional can simply use the remote power source 20 (FIG. 1) to periodically provide sufficient power for the circuitry within the power sensor 110 to ascertain a mean left atrial blood pressure measurement as indicated by whatever sensing component is present within the pressure sensor 110. This mean left atrial blood pressure measurement may be communicated to the remote monitoring device 26 and used for by a physician or the like in monitoring, diagnosing and/or treating the patient.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An implantable mean blood pressure sensor comprising:
    a housing configured to be implanted within a patient;
    a sensing component housed by the housing and exposed to a blood pressure exterior to the housing, wherein in response to the external blood pressure, the sensing component is configured to deform and maintain the deformation in a manner that maintains a mean pressure measurement of the external blood pressure over a period of time of at least one minute; and
    circuitry operatively coupled to the sensing component and responsive to the deformation of the sensing component to produce a mean pressure signal that is representative of the mean pressure of the external pressure over the period of time.

2. The implantable mean blood pressure sensor of claim 1, wherein the circuitry is configured to repeatedly receive an energy transfer from a remote source, and in response, transmit the mean pressure signal back to the remote source.

3. The implantable mean blood pressure sensor of claim 1, wherein the sensing component is configured to deform and maintain the deformation in a manner that maintains the mean pressure measurement of the external pressure over the period of time without the application of electrical power.

4. The implantable mean blood pressure sensor of claim 1, wherein the deformation of the sensing component has a time constant of at least one hour.

5. The implantable mean blood pressure sensor of claim 1, wherein the deformation of the sensing component has a time constant of at least twelve hours.

6. The implantable mean blood pressure sensor of claim 1, wherein the deformation of the sensing component has a time constant of at least 1 day.

7. The implantable mean blood pressure sensor of claim 1, wherein the sensing component comprises:
- a first plate exposed to the external pressure exterior to the housing, the first plate configured to move in response to pressure changes within the external pressure;
- a second plate spaced apart from the first plate and disposed within the housing; and
- a viscoelastic material disposed between the first plate and the second plate.

8. The implantable mean blood pressure sensor of claim 7, wherein the viscoelastic material comprises an electrically non-conductive material, and the mean pressure signal is representative of a capacitance between the first plate and the second plate.

9. The implantable mean blood pressure sensor of claim 7, wherein the viscoelastic material comprises an electrically conductive material, and the mean pressure signal comprises an indication of a resistance between the first plate and the second plate.

10. The implantable mean blood pressure sensor of claim 7, wherein the first plate is electrically conductive and the second plate is electrically conductive.

11. The implantable mean blood pressure sensor of claim 1, wherein the sensing component comprises a hydraulic sensing component.

12. The implantable mean blood pressure sensor of claim 11, wherein the hydraulic sensing component comprises:
- a hydraulic chamber exposed to the external pressure;
- a first fluid disposed within the hydraulic chamber;
- a pressure chamber;
- a second fluid disposed within the pressure chamber;
- a barrier disposed between the first fluid and the second fluid;
- wherein pressure changes in the hydraulic chamber relative to a pressure within the pressure chamber causes movement of the barrier.

13. The implantable mean blood pressure sensor of claim 12, wherein the barrier comprises a low flow valve with a high permeability material.

14. An implantable mean blood pressure sensor that is configured to provide a signal providing an indication of a mean blood pressure value over a period of time, the implantable mean blood pressure sensor comprising:
- a housing configured to be implanted in a patient; and
- a sensing component disposed within the housing yet exposed to an environment exterior to the housing, the sensing component configured to maintain a mean pressure measurement providing an indication of a mean pressure within the environment exterior to the housing over a period of time of at least one minute;
- wherein the sensing component maintains the mean pressure measurement without electrical energy.

15. The implantable mean blood pressure sensor of claim 14, wherein the sensing component comprises a viscoelastic material having a time constant of at least one hour.

16. A left atrial appendage closure device adapted to fit within a patient's left atrial appendage in order to substantially close off the patient's left atrial appendage, the left atrial appendage closure device comprising:
- expandable framework;
- a sensing component exposed to a left atrium pressure within the left atrium of the patient's heart once the left atrial appendage closure device is implanted, wherein in response to the left atrium pressure, the sensing component is configured to deform and maintain the deformation in a manner that maintains a mean pressure measurement of the left atrium pressure over a period of time of at least one minute; and
- circuitry operatively coupled to the sensing component and responsive to the deformation of the sensing component to produce a mean pressure signal that is representative of the mean pressure of the left atrium pressure over the period of time.

17. The left atrial appendage closure device of claim 16, wherein the sensing component comprises a viscoelastic material with a time constant of at least 10 minutes that, in response to the left atrium pressure, viscoelastically deforms in a manner that represents the mean pressure of the left atrium pressure over the period of time.

18. The left atrial appendage closure device of claim 16, wherein the sensing component comprises a hydraulic system including a low flow valve, wherein in response to a positive change in the left atrium pressure, the sensing component moves fluid through the low flow valve under a hydraulic resistance in a first direction subject to a time constant of the sensing component defined at least in part by the low flow valve.

19. The left atrial appendage closure device of claim 18, wherein in response to a negative change in the left atrium pressure, the sensing component moves fluid through the low flow valve in a second direction opposite to the first direction subject to the time constant of the sensing component.

* * * * *